United States Patent [19]
Ron et al.

[11] Patent Number: 5,776,716
[45] Date of Patent: Jul. 7, 1998

[54] METHODS FOR IDENTIFYING AGENTS WHICH BLOCK THE INTERACTION OF FYN WITH PKC-THETA, AND USES THEREOF

[75] Inventors: Dorit Ron; Eugene W. Napolitano. both of San Francisco; Anna Voronova. San Bruno. all of Calif.

[73] Assignee: Terrapin Technologies, Inc.. South San Francisco. Calif.

[21] Appl. No.: 594,447

[22] Filed: Jan. 31, 1996

Related U.S. Application Data

[63] Continuation-in-part of Ser. No. 541,964, Oct. 10, 1995, Ser. No. 473,089, Jun. 7, 1995, Ser. No. 477,346, Jun. 7, 1995, Ser. No. 487,072, Jun. 7, 1995, and Ser. No. 190,802, Feb. 1, 1994, Pat. No. 5,519,003.

[51] Int. Cl.$^6$ .................. C12Q 1/48; C12Q 1/70
[52] U.S. Cl. .................. 435/15; 435/5; 435/7.8
[58] Field of Search .................. 435/15, 5, 7.8

[56] References Cited

U.S. PATENT DOCUMENTS 5,283,173  2/1994  Fields et al. .................. 435/6
5,352,660  10/1994  Pawson .................. 514/12
5,580,979  12/1996  Bachovchin .................. 540/509

FOREIGN PATENT DOCUMENTS

WO 95/21252  1/1995  WIPO .

OTHER PUBLICATIONS

Penninger et al.. Immunol. Rev. 135: 183–214, 1993.
Rickles et al.. EMBO J. 13:5598–5604, 1994.
Baier et al., J.Biol. Chem. 268:4997–5004, 1993.
Dalyrmple, M.A. et al., "The Product of the PRP4 Gene of S. cerevisiae Shows Homology to β Subunits of G Proteins," Cell 58:811–812 (1989).
Dynlacht, B.D. et al., "The dTAF. . 80 subunit of Drosphila TFIID contains β–transducin repeats," Nature 363: 176–179 (1993).
Fong, H.K.W. et al., "Repetitive segmental structure of the transducin β subunit: Homology with the CDC4 gene and identification of related mRNAs," Proc. Natl. Acad. Sci. USA 83: 2162–2166 (1986).
Guillemot, F. et al., "Physical linkage of a guanine nucleotide–binding protein–related gene to the chicken major histocompatibility complex," Proc. Natl. Acad. Sci. USA 86: 4594–459 (1989).
Keleher, C.A. et al., "Ssn6–Tup 1 Is a General Repressor of Transcription in Yeast," Cell 68: 709–719 (1992).
Mochly–Rosen, D. et al., "Identification of intracellular receptor proteins for activated protein kinase C," Proc. Natl. Acad. Sci. USA 88: 3997–4000 (1991).
Mochly–Rosen, D. et al., "Intracellular Receptors for Activated Protein Kinase C," J. Biol. Chem 266(23): 14866–14868 (1991).
Peitsch, M.C. et al., "Sequence similarity of phospholipase A2 activating protein and the G protein β–subunits: a new concept of effector protein activation in signal transduction?," TIBS 18(8): 292–293 (1993).
Ron, D. et al. "An Autoregulatory Region in Protein Kinase C: The Pseudoanchoring Site" Proc. Natl. Acad. Sci. USA 92:492–496 (1995).
Ron, D. et al. "Agonists and Antagonists of Protein Kinase C Function. Derived from its Binding Proteins" J. Biol. Chem. 269:21395–21398 (1994).

(List continued on next page.)

Primary Examiner—Eric Grimes
Attorney, Agent, or Firm—Morrison & Foerster LLP

[57] ABSTRACT

The present invention discloses that the fyn protein binds to the PKC-theta protein. Based on this observation, the present invention provides methods of identifying agents which can be used to modulate immune system activity by blocking fyn/PKC-theta binding and therapeutic methods using such agents.

11 Claims, 10 Drawing Sheets

| | | | | | | INTERACTIONS | |
|---|---|---|---|---|---|---|---|
| | | | | | | PKC theta | PKC delta |
| | | | | K296 | Y417  Y528 | V1  V3 | V3 |
| c-fyn | U | SH3 | SH2 | KINASE | | | |
| 1-258 | U | SH3 | SH2 | | | +   ++ | - |
| 258-534 | | | | KINASE | | ++  ++ | - |

OTHER PUBLICATIONS

Ron, D. et al. "Cloning of an Intracellular Receptor for Protein Kinase C: A Homolog of the Beta Subunit of G Proteins" *Proc. Natl. Acad. Sci. USA* 91:839–843 (1994).

Ruggieri, R., et al. "MSI1, a Negative Regulator of the RAS–cAMP Pathway in Saccharomyces Cerevisiae" *Proc. Natl. Acad. Sci. USA* 86:8778–8782 (1989).

Smith, B.L. and Mochly–Rosen, D., "Inhibition of Protein Kinase C Function by Injection of Intracellular Receptors for the Enzyme," *Biochem. Biophys. Res. Comm.* 188(3): 1235–1240 (1992).

Takagaki, Y. and Manley, J.L., "A Human Polyadenylation Factor Is a G Protein β–subunit Homologue," *J. Biol. Chem* 267(33): 23471–23474 (1992).

Tamaki, M. et al. "Rat Lipocortin I cDNA" *Nucleic Acids Res.* 15:7637 (1987).

van der Voorn, L. and Ploegh, H.L., "The WD–40 repeat," *FEBS Lett.* 307(2): 131–134 (1992).

Wallner, B., et al. "Cloning and Expression of Human Lipocortin, a Phospholipase A2 Inhibitor with Potential Anti–Inflammatory Activity" *Nature* 320:77–81 (1986).

Weinstat–Saslow et al., "A Transducin–like Gene Maps to the Autosomal Dominant Polycystic Kidney Disease Gene Region" *Genomics* 18:709–711 (1993).

Williams, F.E. and Trumbly, R.J., "Characterization of TUP1, a Mediator of Glucose Repression in *Saccharomyces cerevisiae*," *Mol. Cell. Biol.* 10(12): 6500–6511 (1990).

Williams, F.E. et al., "The CYC8 and TUP1 Proteins Involved in Glucose Repression in *Saccharomyces cerevisiae* Are Associated in a Protein Complex," *Mol. Cell. Biol.* 11(6): 3307–3316 (1991).

Derwent Publications Ltd., AN 94–026226 (1994).

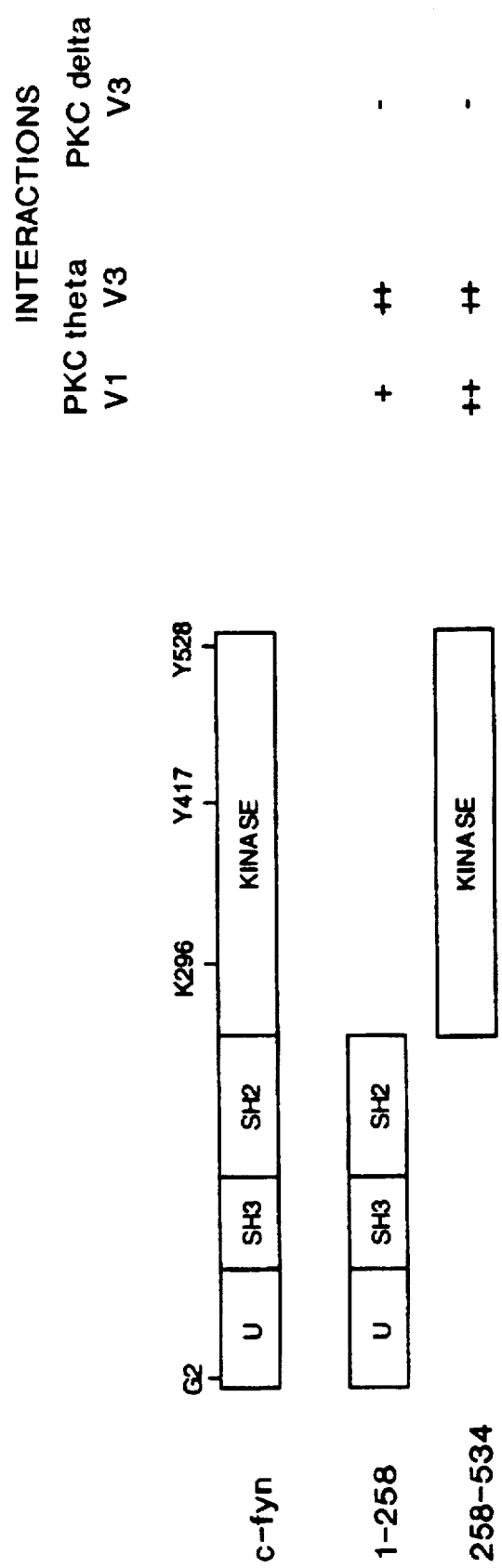

p59 Fyn 1 mgcvqckdke aaklteerdg slnqssgyry gtdptpqhyp sfgvtsipny 50

51 nnfhaaggqg ltvfg<u>gvnss shtgtl</u>rtrg gtgvtlfval ydyartedd lsfhkgekf<u>g ilnsseqd</u>wWea 122

123 rslttgetgyipsnyvapvdsiqaeewyfgklgrk dae<u>rgllsfg</u>nprgtfliresqt tkgay<u>slsird wddm</u> 195

196 kgdhvkhykirkldnggyyittraqetlqqlvq hysekadglcfnltv<u>vsssctpqt</u>Sglakdawevardslfl 270 ekklgqgcfa evwlgtwngn tkvai<u>ktlkpgtmspesf</u>le eaqimkklkh dklvqlyavv seepiyivte
ymskgslldflkdgegralk lpnlvdmaaq vaagmayier mnyihrdlrs anilvgnglickiadfglar liedneytar
qgakfpikwt apeaalygrf tiksdvwsfgilltelvtkg rvpypgmnnr evleqvergyrmpcpqdcpislhelmihc
wkkdpeerptf eylqgfledy ftatepqyqp genl KTLK (bold,underline) = PKC phosphorylation site
underline = RACK1-homologues sequences
Box = WD-40 - like domain

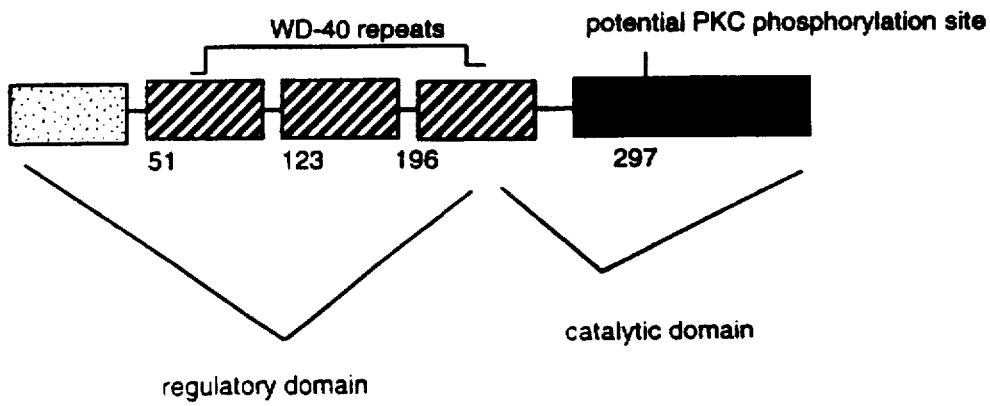

FIG. 10

SEQUENCE LISTING ( 1 ) GENERAL INFORMATION:

( i i i ) NUMBER OF SEQUENCES: 75

( 2 ) INFORMATION FOR SEQ ID NO:1:

( i ) SEQUENCE CHARACTERISTICS:
    ( A ) LENGTH: 532 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Met Gly Cys Val Gln Cys Lys Asp Lys Glu Ala Ala Lys Leu Thr Glu
 1               5                  10                  15
Glu Arg Asp Gly Ser Leu Asn Gln Ser Ser Gly Tyr Arg Tyr Gly Thr
            20                  25                  30
Asp Pro Thr Pro Gln His Tyr Pro Ser Phe Gly Val Thr Ser Ile Pro
             35                  40                  45
Asn Tyr Asn Asn Phe His Ala Ala Gly Gly Gln Gly Leu Thr Val Phe
     50                  55                  60
Gly Gly Val Asn Ser Ser Ser His Thr Gly Thr Leu Arg Thr Arg Gly
 65                  70                  75                  80
Gly Thr Gly Val Thr Leu Phe Val Ala Leu Tyr Asp Tyr Ala Arg Thr
             85                  90                  95
Glu Asp Asp Leu Ser Phe His Lys Gly Glu Lys Phe Gln Ile Leu Asn
            100                 105                 110
Ser Ser Glu Gly Asp Trp Trp Glu Ala Arg Ser Leu Thr Thr Gly Glu
        115                 120                 125
Thr Gly Tyr Ile Pro Ser Asn Tyr Val Ala Pro Val Asp Ser Ile Gln
        130                 135                 140
Ala Glu Glu Trp Tyr Phe Gly Lys Leu Gly Arg Lys Asp Ala Glu Arg
145                 150                 155                 160
Gln Leu Leu Ser Phe Gly Asn Pro Arg Gly Thr Phe Leu Ile Arg Glu
                165                 170                 175
Ser Gln Thr Thr Lys Gly Ala Tyr Ser Leu Ser Ile Arg Asp Trp Asp
            180                 185                 190
Asp Met Lys Gly Asp His Val Lys His Tyr Lys Ile Arg Lys Leu Asp
        195                 200                 205
Asn Gly Gly Tyr Tyr Ile Thr Thr Arg Ala Gln Glu Thr Leu Gln Gln
    210                 215                 220
Leu Val Gln His Tyr Ser Glu Lys Ala Asp Gly Leu Cys Phe Asn Leu
225                 230                 235                 240
Thr Val Ile Ala Ser Ser Cys Thr Pro Gln Thr Ser Gly Leu Ala Lys
                245                 250                 255
Asp Ala Trp Glu Val Ala Arg Arg Ser Leu Cys Leu Glu Lys Lys Leu
            260                 265                 270
Gly Gln Gly Cys Phe Ala Glu Val Trp Leu Gly Thr Trp Asn Gly Asn
        275                 280                 285
Thr Lys Val Ala Ile Lys Thr Leu Lys Pro Gly Thr Met Ser Pro Glu
    290                 295                 300
Ser Phe Leu Glu Glu Ala Gln Ile Met Lys Lys Leu Lys His Asp Lys
305                 310                 315                 320
```

-continued

| | | | | | | | | | | | | | | |
|---|---|---|---|---|---|---|---|---|---|---|---|---|---|---|
| Leu | Val | Gln | Leu | Tyr<br>325 | Ala | Val | Val | Ser | Glu<br>330 | Glu | Pro | Ile | Tyr | Ile<br>335 | Val |
| Thr | Glu | Tyr | Met<br>340 | Ser | Lys | Gly | Ser | Leu<br>345 | Leu | Asp | Phe | Leu | Lys<br>350 | Asp | Gly |
| Glu | Gly | Arg<br>355 | Ala | Leu | Lys | Leu | Pro<br>360 | Asn | Leu | Val | Asp | Met<br>365 | Ala | Ala | Gln |
| Val | Ala<br>370 | Ala | Gly | Met | Ala | Tyr<br>375 | Ile | Glu | Arg | Met | Asn<br>380 | Tyr | Ile | His | Arg |
| Asp<br>385 | Leu | Arg | Ser | Ala | Asn<br>390 | Ile | Leu | Val | Gly | Asn<br>395 | Gly | Leu | Ile | Cys | Lys<br>400 |
| Ile | Ala | Asp | Phe | Gly<br>405 | Leu | Ala | Arg | Leu | Ile<br>410 | Glu | Asp | Asn | Glu | Tyr | Thr<br>415 |
| Ala | Arg | Gln | Gly<br>420 | Ala | Lys | Phe | Pro | Ile<br>425 | Lys | Trp | Thr | Ala | Pro<br>430 | Glu | Ala |
| Ala | Leu | Tyr<br>435 | Gly | Arg | Phe | Thr | Ile<br>440 | Lys | Ser | Asp | Val | Trp<br>445 | Ser | Phe | Gly |
| Ile | Leu<br>450 | Leu | Thr | Glu | Leu | Val<br>455 | Thr | Lys | Gly | Arg | Val<br>460 | Pro | Tyr | Pro | Gly |
| Met<br>465 | Asn | Asn | Arg | Glu | Val<br>470 | Leu | Glu | Gln | Val | Glu<br>475 | Arg | Gly | Tyr | Arg | Met<br>480 |
| Pro | Cys | Pro | Gln | Asp<br>485 | Cys | Pro | Ile | Ser | Leu<br>490 | His | Glu | Leu | Met | Ile<br>495 | His |
| Cys | Trp | Lys | Lys<br>500 | Asp | Pro | Glu | Glu | Arg<br>505 | Pro | Thr | Phe | Glu | Tyr<br>510 | Leu | Gln |
| Gly | Phe | Leu<br>515 | Glu | Asp | Tyr | Phe | Thr<br>520 | Ala | Thr | Glu | Pro | Gln<br>525 | Tyr | Gln | Pro |
| Gly | Glu | Asn<br>530 | Leu | | | | | | | | | | | | |

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

| | | | | | | |
|---|---|---|---|---|---|---|
| Asp<br>1 | Tyr | Lys | Asp | Asp<br>5 | Asp | Lys |

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=epsilon-V1-2

( x i ) SEQUENCE DESCRIPTION: SEQ ID NO:3:

| | | | | | | | |
|---|---|---|---|---|---|---|---|
| Glu<br>1 | Ala | Val | Ser | Leu<br>5 | Lys | Pro | Thr |

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=beta-C2-4

( x i ) SEQUENCE DESCRIPTION: SEQ ID NO:4:

```
Ser  Leu  Asn  Pro  Glu  Trp  Asn  Glu  Thr
1                    5
```

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=beta-C2-1

( x i ) SEQUENCE DESCRIPTION: SEQ ID NO:5:

```
Lys  Gln  Lys  Thr  Lys  Thr  Ile  Lys
1                    5
```

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..13
        ( D ) OTHER INFORMATION: /label=beta-C2-2

( x i ) SEQUENCE DESCRIPTION: SEQ ID NO:6:

```
Met  Asp  Pro  Asn  Gly  Leu  Ser  Asp  Pro  Tyr  Val  Lys  Leu
1                    5                        10
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=beta-C2-3

( x i ) SEQUENCE DESCRIPTION: SEQ ID NO:7:

```
       Ile  Pro  Asp  Pro  Lys  Ser  Glu
        1                  5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /note= "Scrambled beta-C2-1"

( x i ) SEQUENCE DESCRIPTION: SEQ ID NO:8:

```
       Thr  Lys  Gln  Lys  Lys  Ile  Thr  Lys
        1                  5
```

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /note= "Control Peptide"

( x i ) SEQUENCE DESCRIPTION: SEQ ID NO:9:

```
       Leu  Gln  Lys  Ala  Gly  Val  Asp  Gly
        1                  5
```

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=theta-V1-1

( x i ) SEQUENCE DESCRIPTION: SEQ ID NO:10:

```
       Gly  Leu  Ser  Asn  Phe  Asp  Cys  Gly
        1                  5
```

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..11

( D ) OTHER INFORMATION: /label=theta-V1-2

( x i ) SEQUENCE DESCRIPTION: SEQ ID NO:11:

Tyr Val Glu Ser Glu Asn Gly Gln Met Tyr Ile
1               5                   10

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /label=theta-V1-3

( x i ) SEQUENCE DESCRIPTION: SEQ ID NO:12:

Ile Val Lys Gly Lys Asn Val Asp Leu Ile
1               5                   10

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /label=theta-V1-4

( x i ) SEQUENCE DESCRIPTION: SEQ ID NO:13:

Asp Met Asn Glu Phe Glu Thr Glu Gly Phe
1               5                   10

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=delta-V1-1

( x i ) SEQUENCE DESCRIPTION: SEQ ID NO:14:

Ala Phe Asn Ser Tyr Glu Leu Gly Ser
1               5

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
  ( A ) NAME/KEY: Peptide
  ( B ) LOCATION: 1..11
  ( D ) OTHER INFORMATION: /label=delta-V1-2

( x i ) SEQUENCE DESCRIPTION: SEQ ID NO:15:

Ala Leu Ser Thr Glu Arg Gly Lys Thr Leu Val
1               5                       10

( 2 ) INFORMATION FOR SEQ ID NO:16:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..10
    ( D ) OTHER INFORMATION: /label=delta-V1-3

( x i ) SEQUENCE DESCRIPTION: SEQ ID NO:16:

Val Leu Met Arg Ala Ala Glu Glu Pro Val
1               5                   10

( 2 ) INFORMATION FOR SEQ ID NO:17:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..10
    ( D ) OTHER INFORMATION: /label=delta-V1-4

( x i ) SEQUENCE DESCRIPTION: SEQ ID NO:17:

Gln Ser Met Arg Ser Glu Asp Glu Ala Lys
1               5                   10

( 2 ) INFORMATION FOR SEQ ID NO:18:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..7
    ( D ) OTHER INFORMATION: /label=epsilon-V1-1

( x i ) SEQUENCE DESCRIPTION: SEQ ID NO:18:

Asn Gly Leu Leu Lys Ile Lys
1               5

( 2 ) INFORMATION FOR SEQ ID NO:19:

( i ) SEQUENCE CHARACTERISTICS:
    ( A ) LENGTH: 11 amino acids
    ( B ) TYPE: amino acid (C) STRANDEDNESS: single
(D) TOPOLOGY: linear (i i) MOLECULE TYPE: peptide (i x) FEATURE:
   (A) NAME/KEY: Peptide
   (B) LOCATION: 1..11
   (D) OTHER INFORMATION: /label=epsilon-V1-3

(x i) SEQUENCE DESCRIPTION: SEQ ID NO:19:

Leu Ala Val Phe His Asp Ala Pro Ile Gly Tyr
1               5                   10

(2) INFORMATION FOR SEQ ID NO:20:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide (i x) FEATURE:
      (A) NAME/KEY: Peptide
      (B) LOCATION: 1..9
      (D) OTHER INFORMATION: /label=epsilon-V1-4

(x i) SEQUENCE DESCRIPTION: SEQ ID NO:20:

Asp Asp Phe Val Ala Asn Cys Thr Ile
1               5

(2) INFORMATION FOR SEQ ID NO:21:

(i) SEQUENCE CHARACTERISTICS:
      (A) LENGTH: 10 amino acids
      (B) TYPE: amino acid
      (C) STRANDEDNESS: single
      (D) TOPOLOGY: linear (i i) MOLECULE TYPE: peptide (i x) FEATURE:
      (A) NAME/KEY: Peptide
      (B) LOCATION: 1..10
      (D) OTHER INFORMATION: /label=epsilon-V1-5

(x i) SEQUENCE DESCRIPTION: SEQ ID NO:21:

Trp Ile Asp Leu Glu Pro Glu Gly Arg Val
1               5                   10

(2) INFORMATION FOR SEQ ID NO:22:

(i) SEQUENCE CHARACTERISTICS:
      (A) LENGTH: 10 amino acids
      (B) TYPE: amino acid
      (C) STRANDEDNESS: single
      (D) TOPOLOGY: linear (i i) MOLECULE TYPE: peptide (i x) FEATURE:
      (A) NAME/KEY: Peptide
      (B) LOCATION: 1..10
      (D) OTHER INFORMATION: /label=epsilon-V1-6

(x i) SEQUENCE DESCRIPTION: SEQ ID NO:22:

His Ala Val Gly Pro Arg Pro Gln Thr Phe
1               5                   10

(2) INFORMATION FOR SEQ ID NO:23:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..8
   ( D ) OTHER INFORMATION: /label=epsilon-V1-7

( x i ) SEQUENCE DESCRIPTION: SEQ ID NO:23:

Asn Gly Ser Arg His Phe Glu Asp
1               5

( 2 ) INFORMATION FOR SEQ ID NO:24:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..7
      ( D ) OTHER INFORMATION: /label= nu- V1-1

( x i ) SEQUENCE DESCRIPTION: SEQ ID NO:24:

Asn Gly Tyr Leu Arg Val Arg
1               5

( 2 ) INFORMATION FOR SEQ ID NO:25:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..8
      ( D ) OTHER INFORMATION: /label= nu- V1-2

( x i ) SEQUENCE DESCRIPTION: SEQ ID NO:25:

Glu Ala Val Gly Leu Gln Pro Thr
1               5

( 2 ) INFORMATION FOR SEQ ID NO:26:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..11
      ( D ) OTHER INFORMATION: /label= nu- V1-3

( x i ) SEQUENCE DESCRIPTION: SEQ ID NO:26:

Leu Ala Val Phe His Glu Thr Pro Leu Gly Tyr (2) INFORMATION FOR SEQ ID NO:27:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= nu- V1-4

(xi) SEQUENCE DESCRIPTION: SEQ ID NO:27:

Asp Phe Val Ala Asn Cys Thr Leu
1               5

(2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /label= nu- V1-5

(xi) SEQUENCE DESCRIPTION: SEQ ID NO:28:

Trp Val Asp Leu Glu Pro Glu Gly Lys Val
1               5                   10

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= nu- V1-6

(xi) SEQUENCE DESCRIPTION: SEQ ID NO:29:

His Ser Leu Phe Lys Lys Gly His
1               5

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= nu- V1-7

( x i ) SEQUENCE DESCRIPTION: SEQ ID NO:30:

Thr Gly Ala Ser Asp Thr Phe Glu Gly
1               5

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label= mu- V1-1

( x i ) SEQUENCE DESCRIPTION: SEQ ID NO:31:

Met Ser Val Pro Pro Leu Leu Arg Pro
1               5

( 2 ) INFORMATION FOR SEQ ID NO:32:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..11
        ( D ) OTHER INFORMATION: /label= mu- V1-2

( x i ) SEQUENCE DESCRIPTION: SEQ ID NO:32:

Lys Phe Pro Glu Cys Gly Phe Tyr Gly Leu Tyr
1               5                   10

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /label=lambda-V1-1

( x i ) SEQUENCE DESCRIPTION: SEQ ID NO:33:

His Gln Val Arg Val Lys Ala Tyr Tyr Arg
1               5                   10

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..11
    ( D ) OTHER INFORMATION: /label=lambda-V1-2

( x i ) SEQUENCE DESCRIPTION: SEQ ID NO:34:

```
Tyr Glu Leu Asn Lys Asp Ser Glu Leu Leu Ile
1               5                   10
```

( 2 ) INFORMATION FOR SEQ ID NO:35:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..7
    ( D ) OTHER INFORMATION: /label=zeta-V1-1

( x i ) SEQUENCE DESCRIPTION: SEQ ID NO:35:

```
Val Arg Leu Lys Ala His Tyr
1               5
```

( 2 ) INFORMATION FOR SEQ ID NO:36:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=zeta-V1-2

( x i ) SEQUENCE DESCRIPTION: SEQ ID NO:36:

```
Val Asp Ser Glu Gly Asp
1               5
```

( 2 ) INFORMATION FOR SEQ ID NO:37:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=zeta-V1-3

( x i ) SEQUENCE DESCRIPTION: SEQ ID NO:37:

```
Val Phe Pro Ser Ile Pro Glu Gln
1               5
```

( 2 ) INFORMATION FOR SEQ ID NO:38:

( i ) SEQUENCE CHARACTERISTICS:
    ( A ) LENGTH: 9 amino acids
    ( B ) TYPE: amino acid
    ( C ) STRANDEDNESS: single (D) TOPOLOGY: linear (i i) MOLECULE TYPE: peptide (i x) FEATURE:
    (A) NAME/KEY: Peptide
    (B) LOCATION: 1..9
    (D) OTHER INFORMATION: /label=delta-V3-1

(x i) SEQUENCE DESCRIPTION: SEQ ID NO:38:

Gln Gly Phe Glu Lys Lys Thr Gly Val
1               5

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..9
        (D) OTHER INFORMATION: /label=delta-V3-2

(x i) SEQUENCE DESCRIPTION: SEQ ID NO:39:

Asp Asn Asn Gly Thr Tyr Gly Lys Ile
1               5

(2) INFORMATION FOR SEQ ID NO:40:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..9
        (D) OTHER INFORMATION: /label=epsilon-V3-1

(x i) SEQUENCE DESCRIPTION: SEQ ID NO:40:

Ser Ser Pro Ser Glu Glu Asp Arg Ser
1               5

(2) INFORMATION FOR SEQ ID NO:41:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..8
        (D) OTHER INFORMATION: /label=epsilon-V3-2

(x i) SEQUENCE DESCRIPTION: SEQ ID NO:41:

Pro Cys Asp Gln Glu Ile Lys Glu
1               5

(2) INFORMATION FOR SEQ ID NO:42:

( i ) SEQUENCE CHARACTERISTICS:
   ( A ) LENGTH: 9 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..9
   ( D ) OTHER INFORMATION: /label=epsilon-V3-3

( x i ) SEQUENCE DESCRIPTION: SEQ ID NO:42:

Glu Asn Asn Ile Arg Lys Ala Leu Ser
1      5

( 2 ) INFORMATION FOR SEQ ID NO:43:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..8
   ( D ) OTHER INFORMATION: /label=epsilon-V3-4

( x i ) SEQUENCE DESCRIPTION: SEQ ID NO:43:

Gly Glu Val Arg Gln Gly Gln Ala
1      5

( 2 ) INFORMATION FOR SEQ ID NO:44:

( i ) SEQUENCE CHARACTERISTICS:
   ( A ) LENGTH: 15 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..15
   ( D ) OTHER INFORMATION: /label=lambda-V3-1

( x i ) SEQUENCE DESCRIPTION: SEQ ID NO:44:

Met Asp Gln Ser Ser Met His Ser Asp His Ala Gln Thr Val Ile
1    5       10      15

( 2 ) INFORMATION FOR SEQ ID NO:45:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 1..7
   ( D ) OTHER INFORMATION: /label=lambda-V3-2

( x i ) SEQUENCE DESCRIPTION: SEQ ID NO:45:

Leu Asp Gln Val Gly Glu Glu
1      5

( 2 ) INFORMATION FOR SEQ ID NO:46:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label=lambda-V3-3

( x i ) SEQUENCE DESCRIPTION: SEQ ID NO:46:

Glu Ala Met Asn Thr Arg Glu Ser Gly
  1               5

( 2 ) INFORMATION FOR SEQ ID NO:47:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label= mu- V3-1

( x i ) SEQUENCE DESCRIPTION: SEQ ID NO:47:

Asp Pro Asp Ala Asp Gln Glu Asp Ser
  1               5

( 2 ) INFORMATION FOR SEQ ID NO:48:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label= mu- V3-2

( x i ) SEQUENCE DESCRIPTION: SEQ ID NO:48:

Ser Lys Asp Thr Leu Arg Lys Arg His
  1               5

( 2 ) INFORMATION FOR SEQ ID NO:49:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label= mu- V3-3

( x i ) SEQUENCE DESCRIPTION: SEQ ID NO:49:

Ile Thr Leu Phe Gln Asn Asp Thr Gly
1               5

( 2 ) INFORMATION FOR SEQ ID NO:50:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label= mu- V3-4

( x i ) SEQUENCE DESCRIPTION: SEQ ID NO:50:

Gly Ser Asn Ser His Lys Asp Ile Ser
1               5

( 2 ) INFORMATION FOR SEQ ID NO:51:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label=theta-V3-1

( x i ) SEQUENCE DESCRIPTION: SEQ ID NO:51:

Cys Ser Ile Lys Asn Glu Ala Arg Leu
1               5

( 2 ) INFORMATION FOR SEQ ID NO:52:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label=theta-V3-2

( x i ) SEQUENCE DESCRIPTION: SEQ ID NO:52:

Gly Lys Arg Glu Pro Gln Gly Ile Ser
1               5

( 2 ) INFORMATION FOR SEQ ID NO:53:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:

5,776,716

53

54
-continued ( A ) NAME/KEY: Peptide
                ( B ) LOCATION: 1..9
                ( D ) OTHER INFORMATION: /label=theta-V3-3

( x i ) SEQUENCE DESCRIPTION: SEQ ID NO:53:

Asp  Glu  Val  Asp  Lys  Met  Cys  His  Leu
    1                        5

( 2 ) INFORMATION FOR SEQ ID NO:54:

( i ) SEQUENCE CHARACTERISTICS:
                ( A ) LENGTH: 15 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..15
                ( D ) OTHER INFORMATION: /label=zeta-V3-1

( x i ) SEQUENCE DESCRIPTION: SEQ ID NO:54:

Ser  Gln  Glu  Pro  Pro  Val  Asp  Asp  Lys  Asn  Glu  Asp  Ala  Asp  Leu
    1                        5                            10                            15

( 2 ) INFORMATION FOR SEQ ID NO:55:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..7
                ( D ) OTHER INFORMATION: /label=zeta-V3-2

( x i ) SEQUENCE DESCRIPTION: SEQ ID NO:55:

Ile  Lys  Asp  Asp  Ser  Glu  Asp
    1                        5

( 2 ) INFORMATION FOR SEQ ID NO:56:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..9
                ( D ) OTHER INFORMATION: /label=zeta-V3-3

( x i ) SEQUENCE DESCRIPTION: SEQ ID NO:56:

Pro  Val  Ile  Asp  Gly  Met  Asp  Gly  Ile
    1                        5

( 2 ) INFORMATION FOR SEQ ID NO:57:

( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=beta-V3-1

( x i ) SEQUENCE DESCRIPTION: SEQ ID NO:57:

Val Pro Pro Glu Gly Ser Glu Ala
1               5

( 2 ) INFORMATION FOR SEQ ID NO:58:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=alpha-V3-1

( x i ) SEQUENCE DESCRIPTION: SEQ ID NO:58:

Ile Pro Glu Gly Asp Glu Glu Gly
1               5

( 2 ) INFORMATION FOR SEQ ID NO:59:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=gamma-V3-1

( x i ) SEQUENCE DESCRIPTION: SEQ ID NO:59:

Val Ala Asp Ala Asp Asn Cys Ser
1               5

( 2 ) INFORMATION FOR SEQ ID NO:60:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=alpha-V5-1

( x i ) SEQUENCE DESCRIPTION: SEQ ID NO:60:

Gln Leu Val Ile Ala Asn
1               5

( 2 ) INFORMATION FOR SEQ ID NO:61:

( i ) SEQUENCE CHARACTERISTICS:

(A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /label=beta-I-V5-1

(xi) SEQUENCE DESCRIPTION: SEQ ID NO:61:

Lys  Leu  Phe  Ile  Met  Asn
    1                   5

(2) INFORMATION FOR SEQ ID NO:62:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /label=beta-II-V5-1

(xi) SEQUENCE DESCRIPTION: SEQ ID NO:62:

Gln  Glu  Val  Ile  Arg  Asn
    1                   5

(2) INFORMATION FOR SEQ ID NO:63:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /label=delta-V5-1

(xi) SEQUENCE DESCRIPTION: SEQ ID NO:63:

Lys  Asn  Leu  Ile  Asp  Ser
    1                   5

(2) INFORMATION FOR SEQ ID NO:64:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /label=epsilon-V5-1

(xi) SEQUENCE DESCRIPTION: SEQ ID NO:64:

Glu  Ala  Ile  Val  Lys  Gln
    1                   5

( 2 ) INFORMATION FOR SEQ ID NO:65:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label= nu- V5-1

( x i ) SEQUENCE DESCRIPTION: SEQ ID NO:65:

Glu  Gly  His  Leu  Pro  Met
1                        5

( 2 ) INFORMATION FOR SEQ ID NO:66:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=lambda-V5-1

( x i ) SEQUENCE DESCRIPTION: SEQ ID NO:66:

Asp  Asp  Ile  Val  Arg  Lys
1                        5

( 2 ) INFORMATION FOR SEQ ID NO:67:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label= mu- V5-1

( x i ) SEQUENCE DESCRIPTION: SEQ ID NO:67:

Ser  Asp  Ser  Pro  Glu  Ala
1                        5

( 2 ) INFORMATION FOR SEQ ID NO:68:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=theta-V5-1

( x i ) SEQUENCE DESCRIPTION: SEQ ID NO:68:

Arg  Ala  Leu  Ile  Asn  Ser
      1                  5

(2) INFORMATION FOR SEQ ID NO:69:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label=zeta-V5-1

(xi) SEQUENCE DESCRIPTION: SEQ ID NO:69:

Glu  Asp  Ala  Ile  Lys  Arg
      1                  5

(2) INFORMATION FOR SEQ ID NO:70:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label=PRK1-1

(xi) SEQUENCE DESCRIPTION: SEQ ID NO:70:

Gln  Asp  Ser  Lys  Thr  Lys  Ile  Asp
      1                  5

(2) INFORMATION FOR SEQ ID NO:71:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label=PRK2-1

(xi) SEQUENCE DESCRIPTION: SEQ ID NO:71:

Gln  Asp  Ser  Lys  Thr  Lys  Ile  Glu
      1                  5

(2) INFORMATION FOR SEQ ID NO:72:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide (B) LOCATION: 1..8
(D) OTHER INFORMATION: /label=PRK1-2

(xi) SEQUENCE DESCRIPTION: SEQ ID NO:72:

Glu Leu Ala Val Phe Trp Arg Asp
1               5

(2) INFORMATION FOR SEQ ID NO:73:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..8
    (D) OTHER INFORMATION: /label=PRK2-2

(xi) SEQUENCE DESCRIPTION: SEQ ID NO:73:

Glu Ile Ser Val Tyr Trp Arg Asp
1               5

(2) INFORMATION FOR SEQ ID NO:74:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=PRK1-3

(xi) SEQUENCE DESCRIPTION: SEQ ID NO:74:

Met Glu Pro Gln Gly Cys Leu
1               5

(2) INFORMATION FOR SEQ ID NO:75:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=PRK2-3

(xi) SEQUENCE DESCRIPTION: SEQ ID NO:75:

Leu Glu Pro Gln Gly Thr Leu
1               5

METHODS FOR IDENTIFYING AGENTS WHICH BLOCK THE INTERACTION OF FYN WITH PKC-THETA, AND USES THEREOF

RELATION TO OTHER APPLICATION

This application is a continuation-in-part of U.S. Ser. No. 08/541,964, filed 10 Oct. 1995, and U.S. Ser. Nos. 08/473,089, 08/477,346, and 08/487,072, all filed 7 Jun. 1995 and all of which claim priority from PCT Application WO 95/21252 published 10 Aug. 1995. The present application is also a continuation-in-part of U.S. Ser. No. 08/190,802 filed 1 Feb. 1994 now U.S. Pat. No. 5,519,003. The contents of all of the foregoing applications are incorporated herein by reference.

TECHNICAL FIELD

The field of this invention is methods for identifying pharmaceutical agents for use in modulating activities of the immune system and methods of using agents identified in the disclosed methods.

BACKGROUND ART

PCT Application WO 95/21252, discloses and claims peptide compositions which alter the activity of a signal-generating protein with respect to its cognate protein wherein the cognate protein contains at least one WD-40 region which putatively interacts with the signal-generating protein. The peptide compositions mimic the WD-40 regions, thus competing with the interaction of the cognate with the signal-generating protein. This competition results either in inhibiting the signal-generation or activating it.

One specifically exemplified signal-generating protein is protein kinase C (PKC); the illustrated cognate receptor for activated kinase C (RACK), in this case specific for βPKC, was designated RACK1. The gene encoding RACK1 was cloned and sequenced, showing that RACK1 contains the requisite WD-40 regions.

The above PCT application and U.S. Ser. Nos. 08/473,089, 08/477,346, and 8/487,072 further describe methods to identify additional pairs of signal-generating proteins and their cognates and methods for recognizing WD-40 sequences in the cognates. These applications also note that such interactions can be used as a system to identify additional molecules that bind the signal-generating protein by measuring the effect of candidate binding molecules on the interaction between the signal-generating protein and either its cognate per se or the polypeptide compositions that mimic the WD-40 regions of the cognate.

In U.S. Ser. No. 08/541,964, several specific peptides were identified that bind either to the signal-generating protein or to the cognate protein in a signal-affecting manner. The use of the signal-generating protein/cognate system to assay for modulators of signal transduction in assays which are independent of the purity of these participants were described. The PKC enzyme system was illustrated as a specific embodiment. In addition, peptides which reside on the signal-generating protein, as well as those which reside on the cognate or mimics thereof, were described as being useful to modulate the signal-generating interactions and biological activities which are mediated by the signal-generating interactions.

SUMMARY OF THE INVENTION

The present invention is directed to an efficient assay system to identify modulators of intracellular signaling pathways. Because the method takes advantage of inherent biological specificity, it can be conducted on impure preparations of the participants in the signal pathway—the signal-generating protein and its cognate receptor controlling the signal pathway. The assay is conducted by assessing the interaction between the signal-generating protein and its cognate either by measuring binding directly or by measuring a physiological or metabolic effect. The measurement is made in the presence and in the absence of a candidate modulator. Successful candidates which agonize the signal effect an increase in a metabolic or physiological output; antagonists effect a decrease. Both antagonists and agonists compete for binding between cognate and signal-generating protein.

Among successful candidates will be peptides which mimic regions on either the signal-generating protein or the cognate as well as nonpeptide small molecules. Due to their ease of identification, these peptides are particularly useful in alternate forms of the screening assays that detect binding between the peptide and the signal-generating or cognate protein. Although the assay methods disclosed may not all be suitable for direct screening of large chemical libraries, they do enable a sophisticated screening of candidates that can be combined with other techniques for selecting leads.

The methods described herein may involve peptides derived from the cognate or signal-generating protein. By "derived from" we mean that such peptides are either found in the cognate or signal-generating protein, or are modified by a limited number of conservative changes. Preferably the conservative changes represent less than about 20%, more preferably less than about 10%, and most preferably less than about 5% of the residues in the identified native sequence. One way to identify a suitable peptide is to compare sequences among species as is described in Example 4.

The invention is also directed to methods to screen libraries of candidate modulators using the above-described methods and to peptides representative of sites on the signal-generating protein and cognate which are themselves useful in these assays as well as in other applications involving the relevant interaction.

The present invention is also directed to specific embodiments in which the above disclosed methods are employed using the )fyn and PKC-theta protein. Specifically, the fyn protein was found to bind to a PKC protein, namely PKC-theta. Utilizing this interaction, the present invention provides methods to identify modulators of biological and pathological processes which are mediated by fyn/PKC interaction, and methods of modulating such interactions in a subject. Such modulators are useful in modulating an activity of the immune system, particularly the activity and differentiation of T-cells.

The present invention is further based on identifying how fragments of the fyn protein, or related peptides, can be used to bind PKC-theta and modulate activities of the immune system. In the Examples, evidence is presented that the fyn protein binds to PKC-theta. This observation is important because all binding partners of fyn and PKC-theta were previously unknown. The identified fyn/PKC-theta interaction of the present invention can be used as a basis for making and identifying agents which can modulate immune responses. Competitive assays using PKC-theta and the fyn peptide, or a PKC-theta or fyn equivalent, can be used to identify compounds which block fyn/PKC-theta interaction. Additionally, peptide and protein modeling techniques can be used to study the specific interactions of the fyn peptide

BRIEF DESCRIPTION OF THE DRAWINGS

FIGS. 9A and 9B show the regions of fyn (panel A) used in a yeast two hybrid system, and the resulting interactions, are diagrammed in panel B; ++ is a strong interaction (color development in <2 hr), +is a weak interaction (color development within 12 hours), and—is a null interaction (no color at 24 hours). U refers to the Unique sequence portion of fyn; SH3 and SH2 are the src homology domains; kinase is the conserved tyrosine protein kinase catalytic domain.

FIG. 10 (SEQ ID NO: 1) shows a detailed map of sequence motifs present in fyn, including the WD40 repeats, smaller RACK1 homologies, and the most conserved consensus PKC phosphorylation site.

DETAILED DESCRIPTION OF THE INVENTION

I. General Embodiments

The invention is, perhaps, best understood as a generalization of an illustrative interacting signal-generating pair, wherein the signal-generating protein is PKC and the cognate is an appropriate RACK. A peptide that mimics a PKC binding element contained in the RACK or in the PKC or that mimics a RACK-binding element contained in the PKC can be used as a component of assays relevant to the signal pathway.

PKCs represent a family of signal-generating isoenzymes, at least several of which are present in each cell type. Upon activation by a suitable agent, typically phosphatidylserine (PS) and diacylglycerol (DAG), and in some cases calcium ion, a PKC is translocated subcellularly, generally from the soluble fraction to another location in the cell that is associated with the particulate fraction. Each isoenzyme in this family apparently has a cognate anchoring protein at the appropriate location associated with the physiological or metabolic effect of the activation of each particular isoenzyme. Thus, for example, one or a subset of PKCs contained in cardiac myocytes, when activated, results in a slowing of the contraction rate. One or a subset of PKCs contained in Xenopus oocytes, when activated, effect maturation of the egg. One or a subset of PKCs, when inhibited at the catalytic site, blocks T-lymphocyte activation. See, Birdchall et al. (1994) J Pharm. Expt'l Ther. 268:922. The interaction of a particular PKC isoenzyme with its cognate RACK is required for the metabolic or physiological effect; therefore interference with this interaction will modulate that effect. Alternatively, the effect of the modulation may be agonistic if the interaction of the modulator promotes a conformational change in the signal generating partner corresponding to that normally occurring only upon the concurrent binding of activators (e.g., PS or DAG) and cognate protein, or otherwise results in signal activation.

Figure 1:
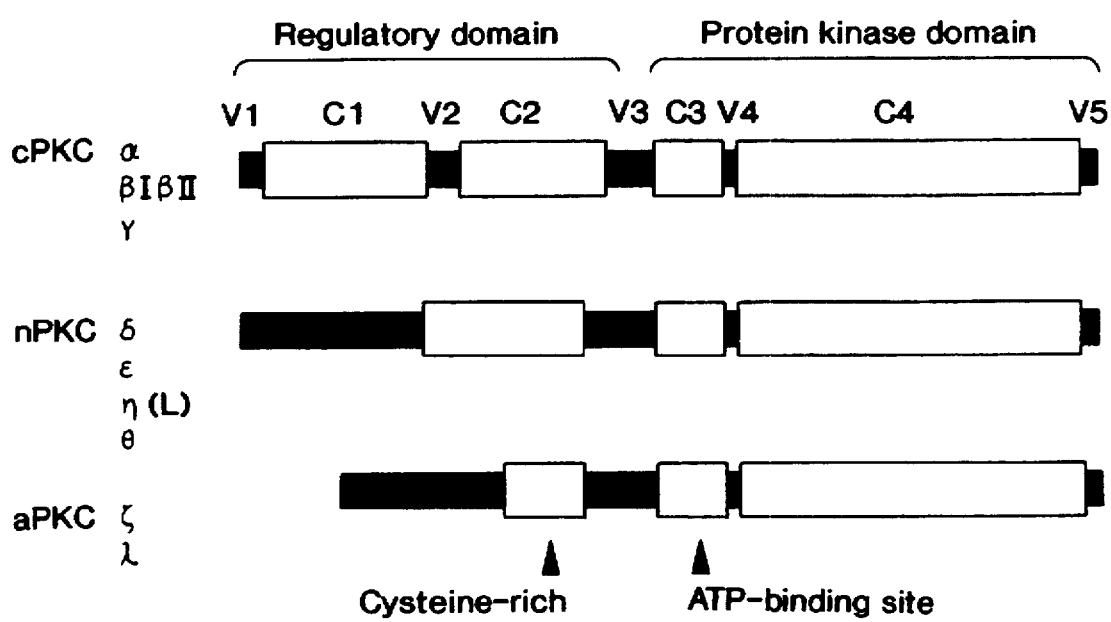
FIG. 1 shows, diagrammatically, the known general primary sequence and domains of various PKC isoenzyme families.

The known PKC isoenzymes can be divided into three major groups as shown in FIG. 1. All of the isoenzymes, regardless of group, contain a protein kinase domain represented by two constant (C) and two variable (V) regions. The regions which are responsible for the enzymatic activity are highly homologous or constant; the C4 region toward the carboxy terminus is thought to contain the catalytic site; the C3 regions upstream are responsible for binding ATP.

Upstream of the protein kinase domain in each case is a regulatory domain. All of the three families, the conventional (cPKC), the novel (nPKC) and atypical (aPKC) contain variable regions at the N-terminus designated V1, and constant regions immediately downstream marked C1. The C1 regions are thought to be involved in activation by phosphatidylserine, diacylglycerol, or pharmacological mimics such as phorbol esters. The C2 region is found only in the cPKC family and is thought to be the site for activation by calcium. However, the picture may not be quite so simple as C1 regions may also be involved in calcium binding, and the atypical class respond poorly to agents such as phorbol esters.

Nevertheless, it now appears clear that sequences within the regions shown as the regulatory domain are responsible for the interaction of the particular PKC with its cognate RACK. They may also contain a RACK-mimicking region, called a pseudo-RACK site, that prevents binding of PKC to its RACK when the PKC has not been activated. This situation is analogous to the pseudosubstrate sequence which is located elsewhere in the primary sequence and blocks the catalytic site prior to activation of the PKC. It is shown hereinbelow that the relevant regions are specific for the particular isoenzyme involved in a designated signal-generation event.

In the parent applications herein, published as PCT WO 95/21252, the cognate RACK1 protein which interacts with βPKC (a member of the cPKC family) was cloned and the WD-40 regions putatively responsible for binding to the βPKC were identified through structural analogy. One of these WD-40 peptides was found to induce the kinase activity of PKC in the absence of PKC activators; both this peptide and another representing a WD-40 region rendered the βPKC susceptible to proteolysis, a characteristic of activated PKC forms. All of these peptides were also shown to inhibit the binding of βPKC to RACK1. In principle, the WD-40 regions of the appropriate RACK can serve as antagonists or agonists of the signal generation associated with the corresponding PKC. As described, an assay which shows the effects of members of a library of candidate modulators on interaction between the relevant PKC and its cognate or the relevant PKC and a WD-40 domain derived from said cognate can be used as a screening assay to identify modulators of this signal pathway.

In the illustrative work described below, similar modulation of signal generation is achieved as before by supplying, to a reaction mixture containing PKC, WD-40 peptides derived from the relevant RACK or pseudo-RACK peptides from the PKC regulatory domain which themselves mimic the RACK's binding domains, and examining the effect of a candidate on binding or signal generation. Similarly, the RACK-binding peptides derived from PKC can be used as assay reagents in combination with the appropriate RACK to screen for modulators of the signal-generating pathway by virtue of the ability of the successful candidate to affect the binding of the cognate protein to the signal-generating protein.

In the second illustrative work described below, PKC-theta is used as the signal-generating protein and WD-40 peptides derived from the fyn protein (the RACK in the above used terminology) are used as the second component.

Thus, in summary, various counterpart interactions can be tested; in no case are purified components required:

| Component 1 | Component 2 | Assay Method |
| --- | --- | --- |
| Signal-generating protein (e.g. PKC) | Cognate protein (e.g. RACK) | binding, outcome (e.g., translocation) |
| " | WD-40 region of e.g. a RACK | binding |
| " | Pseudo-RACK region of PKC | binding |
| RACK-binding region of PKC | Cognate protein, e.g. RACK | binding |
| RACK-binding region of PKC | WD-40 region of RACK | binding |
| RACK-binding region of PKC | Pseudo-RACK region of PKC | binding |
| PKC-theta | fyn | binding |

In general, the present invention is directed to screening methods to identify modulators of particular signal pathways. Each assay will involve identifying a cognate protein that binds sufficiently and specifically to a catalytically active signal-generating protein, via a noncatalytic site, to permit assay in impure preparations (for example fin as the cognate protein and PKC-theta as the signal-generating partner). The interaction of these two components is observed in the presence and absence of a candidate modulator. Depending on the assay system chosen, the interaction and its modification can be observed in a variety of ways, including intracellular binding assays affecting an observable parameter; either a physiological readout, such as change in subcellular distribution, or an artificial construct, such as transcription of a reporter gene, can be used. In no case, however, are purified reagents required, although it may be convenient in some cases, for example, to utilize the peptides identified as illustrated below which represent regions of the signal-generating protein (illustrated by PKC) or its cognate binding protein (represented by the relevant RACK) that are responsible for interaction.

As further described below, the peptides which can be substituted for one or the other component in the assay method are themselves identifiable through conduct of the assay. Thus, the ability of a peptide to affect the interaction of the cognate protein and the signal-generating protein will identify it as a useful component of the assay, as well as a modulator of the signal pathway per se. Once the appropriate peptides are identified, the individual labeled peptides could be used to assess the level of binding. The labeled peptide may represent a region of the signal-generating peptide measured against a composition containing the cognate protein or, conversely, a peptide representing a portion of the cognate protein measured against the composition containing the signal-generating protein. These compositions may be whole cells or cell-free extracts or partially purified extracts.

It will be apparent that when a peptide is chosen as one component of the assay, the screening tests are preferably performed by measuring only binding per se.

Alternatively, both the signal-generating protein and the cognate protein may be contained in a crude preparation and the method for assessing their interaction may include measuring localization of the signal-generating protein within the preparation per se or measuring a metabolic effect of the interaction, such as, for example, maturation of *Xenopus oocytes* or effect on the contraction rate of cardiac myocytes. The particular method of assessing the interaction will, of course, be appropriate to the partners in the interaction, and can readily be ascertained by taking advantage of the specificity of the signal pathways and their components as illustrated below.

Thus, for convenience, the assays to identify modulating candidate compounds will be described as measuring the effect of the candidate on the "binding" of the counterpart components in the reaction mixture. It will be understood that in the instance where both the cognate protein and the signal-generating protein are the active components of the composition participating in the assay, binding may be measured not only directly, but also by the resulting metabolic or physiological effects.

II. Specific Embodiments Directed to the fyn/PKC-theta Interaction

Interaction of fyn with PKC-theta

In the Examples, data are presented which demonstrate that the biological activity of the fyn and PKC-theta proteins are, in part, mediated by the specific interaction of fyn with a member of the PKC family of proteins, namely PKC-theta. Based on these observations, one aspect of the present invention discloses the specific interactions which mediate the biological activities of the fyn and PKC-theta proteins.

As described below, this interaction can be used: 1) to identify and isolate immunomodulating agents, 2) in methods to identify agents which block the association of the fyn protein with PKC-theta, and 3) as a target to rationally design immunomodulating agents Methods to identify agents which block-fyn/PKC-theta interaction.

The present invention further provides methods for identifying agents which modulate immune activity by blocking the fyn /PKC-theta interaction. As provided above, the biological properties of the fyn and PKC-theta proteins are based, in part, on the ability of the fyn protein to bind to a member of the PKC family of proteins, particularly PKC-theta. Knowledge of this interaction provides a basis for identifying therapeutic agents. Such therapeutic agents will be identified as reducing or blocking the association of the fyn protein with PKC-theta.

Specifically, to identify an agent which blocks fyn/PKC-theta interaction, the fyn protein, a fragment of the fyn protein which contains the PKC-theta binding domain, a protein containing the PKC-theta binding domain of the fyn protein, or a cell which expresses the fyn protein or fyn fragment (hereinafter collectively referred to as "the fyn peptide"), is mixed with isolated PKC-theta, an isolated fragment of PKC-theta containing the fyn binding domain, a protein containing the fyn binding domain of the PKC-theta protein, or a cell which expresses the PKC-theta or PKC-theta fragment (hereinafter collectively referred to as "the PKC-theta peptide"), in the presence and absence of an agent to be tested. After mixing under conditions which allow association of the fyn peptide with the PKC-theta peptide, the two mixtures are analyzed and compared to determine if the agent blocked or reduced the amount of binding of the fyn peptide with the PKC-theta peptide. Agents which block or decrease the binding of the fyn peptide with the PKC-theta peptide will be identified as decreasing the amount of binding present in the sample containing the tested agent.

As used herein, an agent is said to block or decrease fyn/PKC-theta binding when the presence of the agent prevents or reduces the amount of association of the PKC-theta peptide with the fyn peptide. One class of agents will reduce or block the association by binding to the PKC-theta peptide while another class of agents will reduce or block the association by binding to the fyn peptide. Two examples of the first class of agent include antibodies which bind to the PKC-theta peptide and block the fyn binding site on PKC-theta and peptides which contain the PKC-theta binding site found on fyn. Two examples of the second class of agents include antibodies which bind to the fyn peptide and block the PKC-theta binding site on fyn and peptides which contain the fyn binding site found on PKC-theta.

The fyn peptide used in the present method can either be the entirely fyn protein whose amino acid sequence is known in the art, a fragment of the fyn peptide which binds the PKC-theta, or a protein which contains the PKC-theta binding site of fyn, such as a fusion protein containing the fyn sequence. Alternatively, the fyn peptide can contain more than one copies of the fyn sequence, such as in a palindromic or tandem repeat. Lastly, a cell or virus expressing the fyn peptide can be used.

As an alternative to compounds containing the fyn sequence, agents identified in the present method can be substituted for the fyn peptide. For example, an agent which is found to block fyn/PKC-theta binding by binding to PKC-theta can be used in place of the fyn peptide.

The PKC-theta peptide used in the present method can be any isolated member of the PKC-theta family of proteins so long as the member binds the fyn peptide. As used herein, a PKC-theta family member refers to proteins currently known in the art which are members of the PKC-theta family of proteins (for a review see Baier et al *J. Biol. Chem.* 268(7):4997–5004 (1993) and Baier et al., *Eur. J. Biochem.* 225(1):195–203 (1995)). These include PKC-theta isolated from organisms such as humans, mice, etc., as well as the various splice forms of PKC-theta found in each organism. The PKC-theta family member can be used in its entirety or a fragment of the PKC-theta protein which contains the fyn binding site can be used. The preferred fragment will be derived from the V1 or V3 regions of PKC-theta. Alternatively, a cell or virus expressing the PKC-theta, or PKC-theta fragment, can be used.

The fyn and PKC-theta peptides used in the present invention can be used in a variety of forms. The peptides can be used in a highly purified form, free of naturally occurring contaminants. Alternatively, a crude preparation containing a mixture of cellular components as well as the fyn and PKC-theta peptides can be used. Further, the fyn or PKC-theta peptides can be isolated from cells which naturally express these peptides, from cells which have been altered, using recombinant methods, to express these peptides, or can be synthesized using standard peptide synthesis methods. So long as the association of the PKC-theta peptide with the agent to be tested and/or the fyn peptide can be identified in the sample, the fyn and PKC-theta peptides are in a suitable form for use in the above described assay.

The fyn and/or PKC-theta peptides can additionally be modified to contain a detectable label or signal generation system to facilitate detection. Methods for attaching agents such as fluorescence tags or fluorescence polarization and secondary labeling agents such as biotin, are well known in the art.

A variety of art known methods can be adapted and employed to detect whether an agent blocks or reduces the interaction of the fyn peptide with the PKC-theta peptide. Such methods include, but are not limited to, assays which employ a solid support, assays in solution phase, assays performed in a gel-type media, and assays which use a combination of these environments. An example of a solid phase assay would be one in which one or both of the fyn and PKC-theta peptides are immobilized on a solid support and is incubated in a solution phase with the agent to be tested and the other peptide of the fyn/PKC-theta pair. A secondary detection means, such as an antibody, is then used to determine the amount of the second peptide which binds to the immobilized peptide. Alternatively, the second peptide of the fyn /PKC-theta pair can be detectably labeled and its binding to the immobilized first peptide is directly assessed. One format which is preferably suitable for a solid phase based assay is immobilization of one of the peptides in a 96-well micro-titer plate. Such titer plates provide an efficient assay format for rapidly processing multiple samples.

Alternatively, both peptides of the fyn/PKC-theta binding pair can be in solution. After mixing, the binding of the fyn peptide to the PKC-theta peptide can be detected using a variety of methods, for example detecting mobility shifts using electrophoretic means. One skilled in the art can readily appreciate how numerous assay-type formats which are known in the art for use in competitive assays can be modified to use the fyn/PKC-theta peptide pair.

Direct binding to the PKC-theta peptide or the fyn peptide can be used as first step in identifying agents which block fyn/PKC-theta interaction. In such methods, agents are first screened for the ability to bind to the PKC-theta or fyn peptides. Agents which bind to either of the two peptides are then screened for the ability to block fyn/PKC-theta interaction, or for the ability to modulate a function of the immune system.

Agents which are assayed in the above methods can be randomly selected or rationally selected or designed. As used herein, an agent is said to be randomly selected when the agent is chosen randomly without considering the specific sequences involved in the association of the fyn peptide with the PKC-theta peptide. An example of randomly selected agents is the use of a chemical library or a peptide combinatorial library.

As used herein, an agent is said to be rationally selected or designed when the agent is chosen on a nonrandom basis which takes into account the sequence of the target site and/or its conformation in connection with the agent's action. As described above, two sites of actions for agents of the present invention are the fyn peptide and the PKC-theta peptide. Agents can be rationally selected or rationally designed by utilizing the peptide sequences which make up the contact sites of the fyn/PKC-theta pair. For example, a rationally selected peptide agent can be a peptide whose amino acid sequence is identical to the fyn contact site found on PKC-theta. Such an agent will reduce or block the association of fyn with PKC-theta by binding to fyn.

The agents of the present invention can be peptides, small molecules, vitamin derivatives, as well as carbohydrates. A skilled artisan can readily recognize that there is no limit as to the structural nature of the agents of the present invention or those used in the present assay methods.

As provided above, one class of agents of the present invention are peptide agents whose amino acid sequences is chosen based on the amino acid sequence of fyn and in particular the PKC-theta contact site found on fyn, while a second class of agents of the present invention are peptide agents whose amino acid sequences is chosen based on the amino acid sequence of PKC-theta and in particular the fyn contact site found on PKC-theta. The fyn contact site on PKC-theta and the PKC-theta contact site on fyn can readily be determined using art-known methodologies. For example, tryptic digestion of the PKC-theta protein can be performed and the various fragments of PKC-theta can be tested for their ability to bind the fyn peptide. Alternatively, a modification of a bind and chew assay can be used in which the fyn and PKC-theta peptides are allowed to interact and the interactive pair is subject to protein digestion. Regions of the PKC-theta peptide which are contacted by the fyn peptide will be protected from digestion and can be later characterized to determine the amino acid sequence which is bound and protected.

All of the peptide agents of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1–6C. In all of the peptides of the invention, one or more amide linkages (—CO—NH—) may optionally be replaced with another linkage which is an isostere such as —$CH_2NH$—, —$CH_2S$—, —$CH_2CH_2$, —CH=CH—(cis and trans), —$COCH_2$—, —CH(OH) $CH_2$—and —$CH_2SO$—. This replacement can be made by methods known in the art. Alternative peptide linking moieties can also be used to decrease the rate of degradation of peptide based agents. The following references describe preparation of peptide analogs which include these alternative-linking moieties: Spatola, A. F., *Vega Data* (Mar. 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Spatola, A. F., et al., *Life Sci* 38:1243–1249 (1986)(—$CH_2$—S); Hann, M. M., *J Chem Soc Perkin Trans I* 307–314 (1982) (—CH—CH—, cis and trans); Almquist, R. G., et al., *J Med Chem* 23:1392–1398 (1980) (—$COCH_2$—); Jennings-White, C., et al., *Tetrahedron Lett* 23:2533 (1982)(—$COCH_2$—); Holladay, M. W., et al., *Tetrahedron Lett* 24:4401–4404 (1983)(—C(OH)$CH_2$—); and Hruby, V. J., *Life Sci* 31:189–199 (1982)(—$CH_2$—S—).

Another class of agents of the present invention are antibodies immunoreactive with critical positions of the fyn protein or with the PKC-theta protein. Since the target for action of the agents of the present invention is within a cell (cell signaling involved in fyn/PKC-theta interaction), antibody agents are useful in immunodiagnostic methods and find use as substitutes for either the fyn or PKC-theta peptides in the present methods.

Antibody agents are obtained by immunization of suitable mammalian subjects with peptides, containing as antigenic regions, those portions of the fyn or PKC-theta proteins which are intended to be targeted by the antibodies. Critical regions include, but are not limited to, the contact sites involved in the association of fyn with PKC-theta and sites which provide steric interference with the contact sites upon binding.

Antibody agents are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at the amino or carboxy terminus with a cysteine residue or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. (See Harlow: Antibodies Cold Spring Harbor Press NY 1989) The immortalized cell lines secreting the desired antibodies are screened by immunoassay in which the antigen is the peptide hapten or is the PKC-theta or fyn peptide. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of $F(ab')_2$ fragments is often preferable, especially in a therapeutic context, as these fragments are generally less immunogenic than the whole immunoglobulin. The antibodies or fragments may also be produced, using current technology, by recombinant means. Regions that bind specifically to the desired regions of receptor can also be produced in the context of chimeras with multiple species origin.

Uses for Agents which Block the Association of fyn with a Member of the PKC-theta Family of Proteins The fyn and PKC-theta proteins have been implicated in modulating a variety of biological responses. The present invention discloses that the interaction of these two proteins are involved in modulating activities of the immune system, particularly responses involving T-cell activity. Therefore, agents which block or reduce fyn/PKC-theta binding can be used to modulate activities of the immune system.

Specifically, immune system activity, such as T-cell mediated responses, can be modulated by administering to a subject an agent which blocks the interaction of the fyn peptide with the PKC-theta peptide. As used herein, a subject can be any mammal, so long as the mammal is in need of modulation of immune activity. The term "mammal" is meant an individual belonging to the class Mammalia. The invention is particularly useful in the treatment of human subjects.

As used herein, immune system activity refers to the wide variety of cellular events in which cells of the immune system participate. Examples of situations where it is desirable to modulated such activity include, but are not limited to, transplant surgery and autoimmune disorders. In each of these situations, it is desirable to selectively reduce T-cell responsiveness.

As used herein, an agent is said to modulate an immune system activity, or reduce the severity of a pathological condition mediated by the immune system, when the agent prevents the normal immune activity of the subject. For example, an agent is said to modulate graft rejection when the agent reduces the rate of onset of graft rejection or reduces the severity of graft rejection.

Administration of Agents which Modulate Immune System Activity

The agents of the present invention can be provided alone, or in combination with another agent that modulates a function of the immune system. For example, an agent of the present invention used to reduce T-cell activity can be administered in combination with other immunosuppressive agents. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents of the present invention. While individual needs vary, determination of optimal ranges of effective amounts of each component is within the skill of the art. Typical dosages comprise 0.1 to 100 mg/kg/body wt. The preferred dosages comprise 1 to 100 mg/kg/body wt. The most preferred dosages comprise 10 to 100 mg/kg/body wt.

In addition to the pharmacologically active agent, a composition comprising an agent of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

Methods for Targeting the Pharmaceutical Agents of the Present Invention

The present invention further provides methods for increasing the affinity of the agents of the present invention, as well as other known agents which block or reduce fyn/PKC-theta interaction. Specifically the affinity of an agent which blocks the fyn/PKC-theta interaction can be increased by covalently linking the agent to a second agent which has a equal or higher affinity for either PKC-theta or fyn. Such a second agent will bind to another site on either the fyn or PKC-theta molecule and bring the fyn/PKC-theta blocking agent into close proximity to the target site. Such second agents can be, but are not limited to, antibody and peptide agents. The second agent can be covalently attached to the fyn/PKC-theta blocking agent using art know methods. Methods which employ linkers are particularly well suited for this use.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLE 1

Specificity of Negative Chronotropy for εPKC Translocation

Neonatal rat cardiac myocytes were used in this assay. These cells, when prepared in culture, exhibit contractions at approximately the rate of 40–50/15 sec., and it is known that the phorbol ester, 4β-phorbol 12-myristate-1 3-acetate (PMA) reduces the contraction rate (Johnson, J. A. et al., *Circ Res* (1995) 76:654–653). Previous work has also shown that treating cardiac myocytes with PMA or with norepinephrine (NE) causes translocation of αPKC to the nuclear boundary, βIPKC to the interior of the nuclei, δPKC to the fibrillar and perinuclear structures, and εPKC to cross-striated structures (Disatnik, M-H. et al., *Exp Cell Res*

(1994) 210:287–297). It has also been shown that exogenously added activated PKCs bind similarly (Mochly-Rosen, D. et al., *Molec Biol Cell* (1990) 1:693–706). Since the location to which the various isoenzymes are translocated are different, it has been suggested that the variable regions specific for each isoenzyme (Nishizuka, Y., *Nature* (1988) 334:661–665) should contain at least part of the specific RACK binding site (Disatrik, M-H. et al., *Exp Cell Res* (1994) 210:287–297). Furthermore, it has been suggested that the V1 region of εPKC determines its substrate specificity (Pears, C. et al., *Biochem J* (1991) 276:257–260).

To show that only translocation of the corresponding isoenzyme is inhibited by one of its fragments—e.g., only translocation of εPKC is inhibited by an εPKC-V1 fragment, cells cultured on chamber slides were permeabilized with saponin (50 μg/ml) in the absence or presence of 100 μg/ml rat recombinant εPKC-V1 or δPKC-V1 fragments containing amino acids 2–144 in each case. Cellular functions, including cell viability, spontaneous and stimulated contraction rates, gene expression and hypertrophy are unaffected by the saponin treatment.

These fragments were prepared by amplifying the relevant portion of the gene from a cDNA library (Stratagene). A FLAG™ epitope (DYKDDDK(SEQ ID NO: 2)) was engineered at the 5' end of the fragment and the 0.45 kb PCR fragment was subcloned into pMAL-C2 vector (New England Biolabs) for overexpression as a fusion protein with maltose binding protein in *E. coli*. Protein purification and Factor Xa proteolysis of the fusion proteins was as described by Ron, D. et al., *Proc Natl Acad Sci USA* (1994) 91:839–843.

The intracellular concentration of each fragment was approximately 300 nM or about 3% of the extracellular concentration as determined by quantitative Western blot of washed and extracted cells.

After the εPKC-V1 or δPKC-V1 fragments were administered by permeabilization, the cells were incubated with either 4-α or 4-βPMA. (4αPMA is not active and is used as a control.) The cells were then fixed with methanol and acetone and PKC isoenzyme localization was determined by immunofluorescence; the antisera used to detect δPKC and εPKC do not recognize the administered fragments. Multiple fields of cells for each treatment group and for PKC isoenzymes α, βI, δ, and ε were observed and the data were presented as a percentage of cells having the tested enzyme at the activated site. When the cells were treated with 100 nM PMA for five minutes, it was apparent that neither δPKC-V1 nor εPKC-V1 had any effect on translocation of the α or β isoenzymes whereas each of the δ and ε fragments specifically inhibited the translocation of the corresponding isoenzyme, but not the other isoenzyme. An additional experiment measuring translocation of εPKC at the much lower level of 3 nM PMA also showed complete inhibition by the ε fragment. It has previously been shown that 3 nM PMA is only marginally effective in translocation of PKC isoenzymes other than the ε form (Johnson, J. A. et al., *Circ Res* (1995) 76:654–663).

Figure 2A:
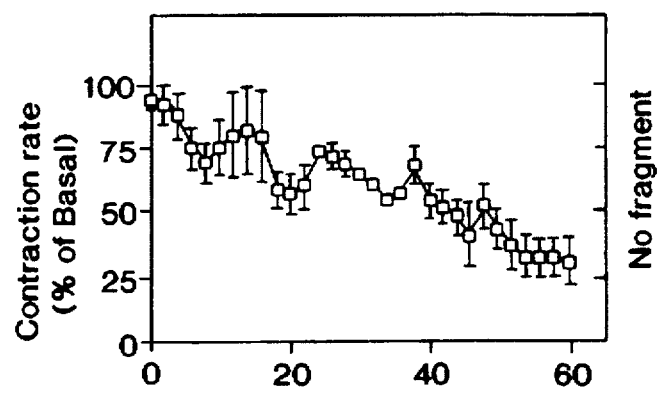
FIGS. 2A, 2B and 2C show the result of experiments demonstrating that PKC mediated effects on contraction of cardiac myocytes is inhibited by a fragment of the regulatory domain of εPKC but not by a corresponding fragment of δPKC.
Figure 2B:
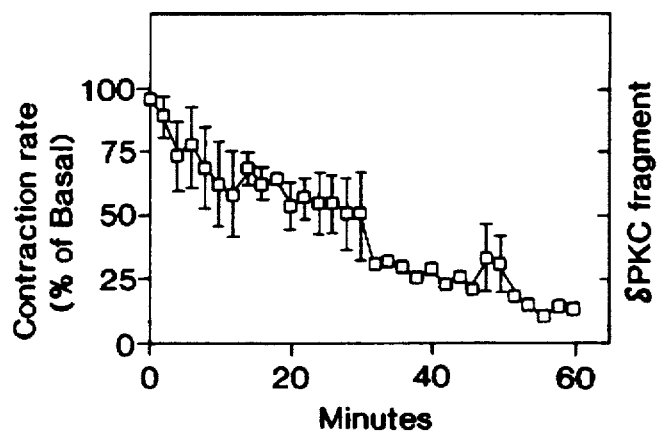
Figure 2C:
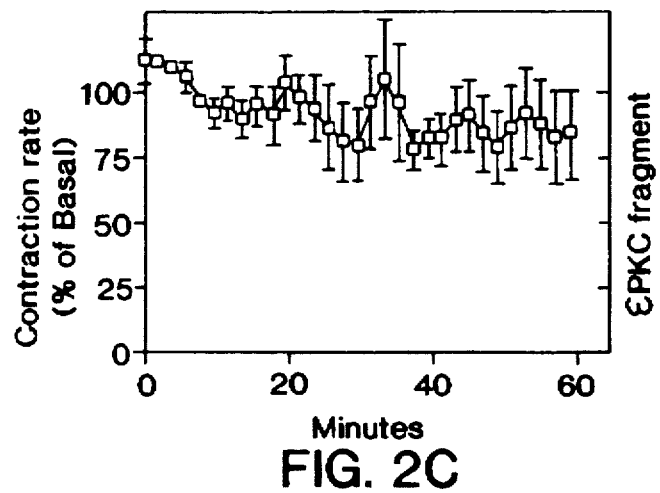

The localization of εPKC to the cross-striated structures suggested that the ε isoenzyme might mediate the effect of PMA on the contraction rate. Cells were cultured and permeabilized with saponin in the presence or absence of 150 μg/ml δ or εPKC-V1 fragments described above. Basal contraction rates were monitored for 10 min., and the cells were then treated with 3 nM PMA. The rate of contraction was monitored over the next 20 minutes. The results are shown in FIG. 2.

As shown, in cells where no fragment was added, the contraction rate is reduced almost to zero within 15 min of the addition of PMA. Similarly, in cells where the δPKC fragment is added, the contraction rate is thus reduced. However, in cells where the εPKC fragment was added, the contraction rate is maintained. Thus, the εPKC-V1 fragments specifically prevented PMA-induced inhibition of spontaneous contraction. These data, combined with the data described above with respect to translocation and the fact that the εPKC-V1 fragment does not affect the catalytic activity of εPKC in vitro, demonstrate that the translocation of εPKC is an essential step in signaling the chronotropic effect of PMA and that this signaling is inhibited by a fragment containing the V1 region.

The effect of PMA in reducing the contraction rate can be mimicked by controlling the α1 and β1 adrenergic receptors of the myocytes, providing a more physiologically relevant phenomenon. If both the α1 and β1 receptors are activated with NE, an increase in contraction rate occurs; when both receptors are inhibited, NE no longer has this effect. If the α1 receptor is inhibited alone by prazosin, the initial increase in contraction rate is higher; if the β1 receptor alone is inhibited, the contraction rate decreases.

When either the δ or ε fragments described above is substituted for the known inhibitors of the α1 and β1 receptors, the behavior of the cells in response to NE is unaffected by the presence of the δ fragment; however, addition of the ε fragment gives a response similar to that obtained in the presence of prazosin. These data are consistent with the role of the ε fragment in controlling contraction rate since the α1 receptor (inhibited by prazosin) mediates PKC translocation.

Figure 3:
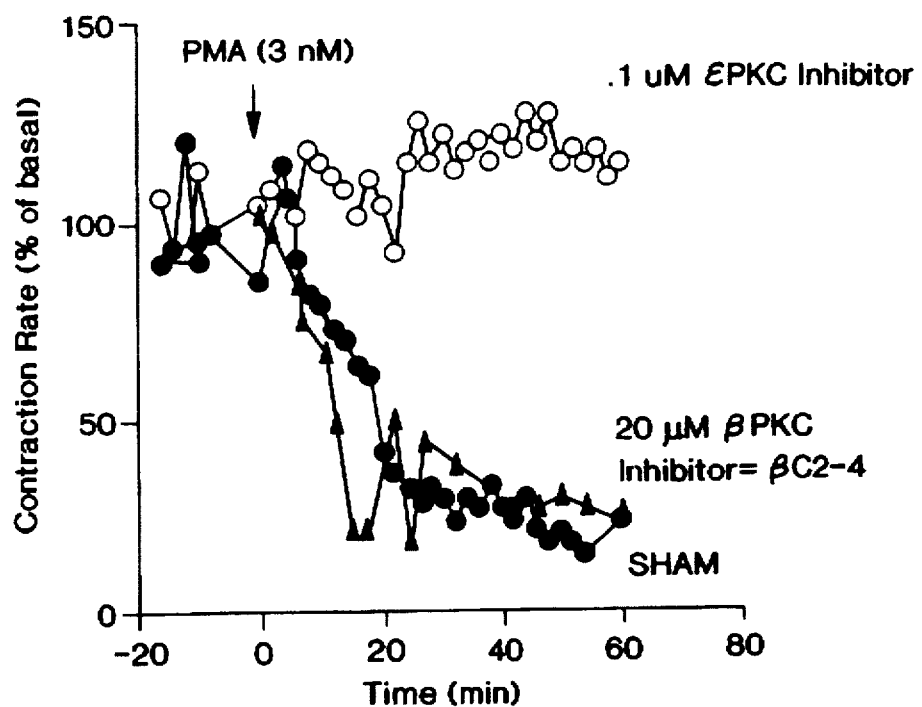
FIG. 3 shows the specific effect of an 8 amino acid peptide derived from the RACK-binding site in the regulatory domain of εPKC on the contraction rate of cardiac myocytes; an analogous peptide from the βPKC has no effect.

FIG. 3 shows the results of a similar experiment using stimulation with 3 nM PMA, and providing peptides of less than 10 residues that block localization of εPKC and βPKC using a 0.1 μM εPKC-derived peptide εV1-2 (sequence EAVSLKPT (SEQ ID NO: 3)) or 20 μM of a βPKC-derived peptide βC2-4 (sequence SLNPEWNET (SEQ ID NO: 4)). As shown in FIG. 3, stimulation with 3 nM PMA without adding peptides to the permeabilized cells or in the presence of 20 μM of the βPKC localization inhibitor results in negative chronotropy as above.

EXAMPLE 2

Specific Inhibition of βPKC Translocation by C2-Derived Peptides

The parent application herein described binding sites on a particular RACK, RACK1, which are responsible for binding βPKC. It is recognized that if the binding site on PKC is identified, peptides that mimic this binding site could also serve as modulators of βPKC translocation and function. Furthermore, it should be noted that PKC may itself contain pseudo-RACK peptide sequences that mimic the binding sites on RACK and regulate the exposure of the binding site for RACK on PKC. The following experiments do not distinguish between these possibilities; nevertheless, whichever function on the PKC sequence is represented, mimics of the sequence will be effective modulators of the relevant signal pathway.

The cPKC class of isozymes comprises the only members of the PKC general family that contains C2 regions. Other C2-containing proteins such as synaptotagmin and phospholipase Cγ also bind to a mixture of RACKs prepared from cell particulate fractions. It has also been demonstrated that recombinant fragments of synaptotagmin containing the C2 homologous region bind to mixtures of RACKs and inhibit PKC binding to RACKs (Mochly-Rosen, D. et al., *Biochemistry* (1992) 31:8120–8124).

The following experiments demonstrate that certain peptides residing in the C2 region of βPKC are able to inhibit translocation of βPKC and the maturation of *Xenopus* oocytes.

The following βPKC-derived peptides were prepared:

βC2-1 (SEQ ID NO: 5): KQKTKTIK (210–217);
βC2-2 (SEQ ID NO: 6): MDPNGLSDPYVKL (186–198);
βC2-3 (SEQ ID NO: 7): IPDPKSE (201–207);
βC2-4 (SEQ ID NO: 4): SLNPEWNET (218–226);
Scrambled βC2-1 (SEQ ID NO: 8): TKQKKITK;
Control Peptide (SEQ ID NO: 9): LQKAGVDG (266–271).

Recombinantly produced fragments of βPKC were expressed as fusion proteins with GST: Fusion L9 includes the V1 region, the pseudosubstrate sequence, and the C1 and V2 regions (residues 3–182) of βPKC. L10 includes the $V_1$ region, the pseudosubstrate sequence and the first cysteine repeat from the C1 region, as well as the entire C2 and V3 regions (residues 3–76 and 143–339). The numbering is as described in Luo, J-H. et al., *J Biol Chem* (1993) 248:3715–3719.

Standard overlay assays were performed by blotting RACK1 onto nitrocellulose as described by Mochly-Rosen, D. et al, *Proc Natl Acad Sci USA* (1991) 88:3997–4000. Strips of the nitrocellulose sheet containing 0.1–1 μg RACK1 per strip were incubated in overlay buffer with or without the test fragment added at approximately 10 μM. Addition was in the presence or absence of 50 μg/ml phosphatidyl serine (PS) and 1 mM calcium. The mixture was further incubated for 30 min at room temperature. The strips were then washed and binding of fragment of L9 or L10 to RACK1 was detected with anti-GST polyclonal antibodies followed by labeling with anti-rabbit horseradish peroxidase-linked antibodies and development by addition of substrate.

Using this assay, L10, but not L9 was found to bind RACK1. The PKC activators phosphatidyl serine and calcium did not increase the binding of L10 to RACK1, although these activators are necessary for the binding of intact PKC to RACK1. Thus, these data are consistent with the suggestion that the PKC activators are required to expose the RACK binding site in the intact PKC; this site is already exposed in the C2-containing fragment L10.

To determine whether L10 would inhibit the binding of intact βPKC to RACK1, RACK1 was immobilized on an amylose column and βPKC binding in the presence of PS, DAG and calcium and in the presence of L10 or L9 was determined. In the presence of L10, βPKC binding to RACK1 was completely inhibited; however, this was not true of L9. Similar results were obtained in an overlay assay.

Similar overlay assays were conducted using the above-listed peptides as candidate inhibitors for the binding of L10 to RACK1. The C2-derived peptides βC2-1, βC2-2 and βC2-4 peptides were successful in inhibiting binding of L10 to RACK1; however βC2-3 and scrambled βC2-1 were not.

In addition to the foregoing cell-free assays, the association of βPKC with RACK1 and the ability of peptides derived from the C2 region to interrupt this interaction was tested in rat neonatal cardiac myocytes in culture. The presence of RACK1 in these cells was confirmed by immunostaining. RACK1 was found at perinuclear structures and throughout the cytosol. Treating with NE or PMA did not alter these locations. It was also demonstrated that activated βII PKC, but not C2-less isoenzymes δ or εPKC, colocalized with RACK1.

The C2-derived peptides that had been shown to inhibit βPKC binding to RACK1 in vitro were then tested for their ability to inhibit activation-induced translocation in myocytes.

The myocytes were exposed to 100 nM PMA for 15 min after transient permeabilization with saponin (50 μg/ml) in the presence and absence of the test peptides. 80% of the cells that had not been treated with peptides showed localization of β1 PKC to perinuclear structures. However, when βC2-1, βC2-2 or 10 C2-4 at 10 μM extracellular concentration had been supplied to the permeabilized cells, translocation of both 1 PKC and II PKC isoenzymes was inhibited by 65–95%. βC2-4 was the most effective. Control peptides described above did not affect translocation.

Consistent with the results in Example 1, treating non-permeabilized cardiac myocytes with 100 nM PMA resulted in translocation of εPKC from the nucleus to the perinuclear and cross-striated structures and of δPKC from the perinuclear and fibrilar cytosolic structures in 80% and 90% of the cells respectively. Permeabilization and treatment of the cells with the C2 peptides derived from βPKC had no effect on the translocation of these C2-less isozymes.

While the chronotropy of myocytes is not affected by βPKC isoenzymes, the insulin-induced maturation of *Xenopus oocytes* is mediated by the 62 form. Insulin treatment of these *oocytes* results in translocation of βPKC and maturation is delayed by the PKC-specific catalytic inhibitor pseudosubstrate peptide. PKC translocation is blocked by injection of purified RACKs or a peptide corresponding to the PKC binding site on RACKs. (Smith, B. L. et al., *Biochem Biophys Res Commun* (1992) 188:1235–1240; Ron, D. et al., *J Biol Chem* (1994) 269:21395–21398).

Figure 4:
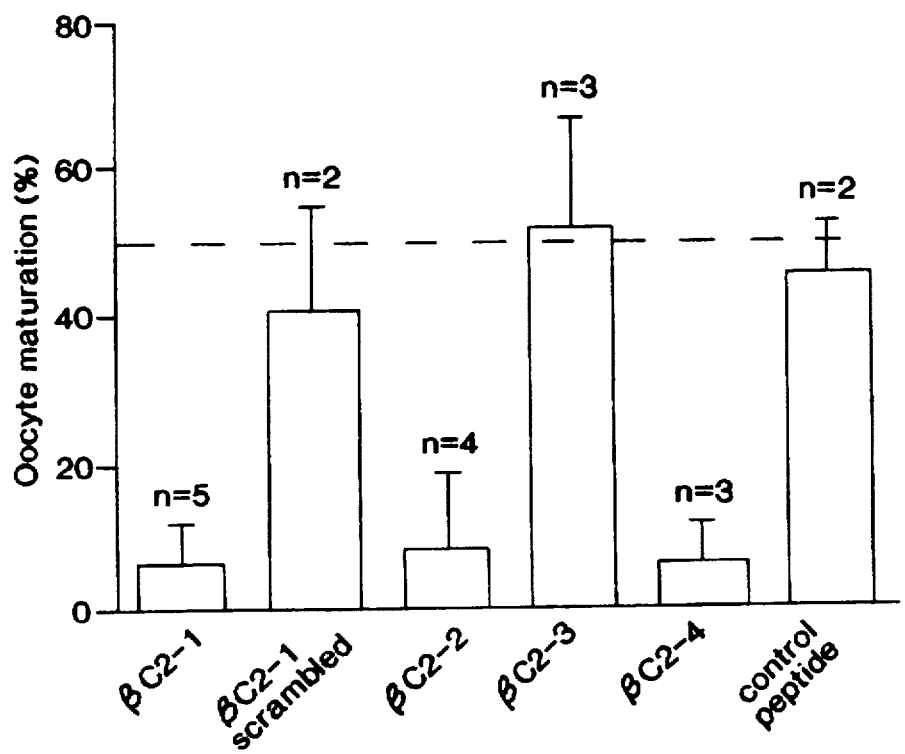
FIG. 4 shows the specific effect of peptides derived from the RACK-binding site of βPKC on maturation of Xenopus oocytes.

Accordingly, the maturation of *Xenopus oocytes* was used as an alternative assay system to test the function of the peptides derived from the C2 region described above. In this assay, oocytes were injected with 50 μM of the test peptide one hour before insulin treatment (8.25 μg/ml). Insulin-induced *oocyte* maturation was then determined by monitoring the appearance of a white spot in the animal pole of the *oocyte* that is indicative of germinal vesicle breakdown in maturation. 10–15 oocytes were included per assay and oocytes were scored for 35 hours after treatment. As expected, βC2-1, βC2-2 and βC2-4 supplied in the range of 5 μM–500 μM significantly delayed oocyte maturation in a dose-dependent manner. The control peptides did not. The association of this effect with the prevention of translocation of βPKC to the particulate fraction in *Xenopus oocytes* was confirmed in a separate experiment. The peptide ,βC2–4 inhibited βPKC translocation but not θPKC in T-JurkaT-cells. FIG. 4 shows the effect of these various peptides on *Xenopus oocyte* maturation.

EXAMPLE 3

Agonist Effect of Interacting Peptides

Figure 5A:
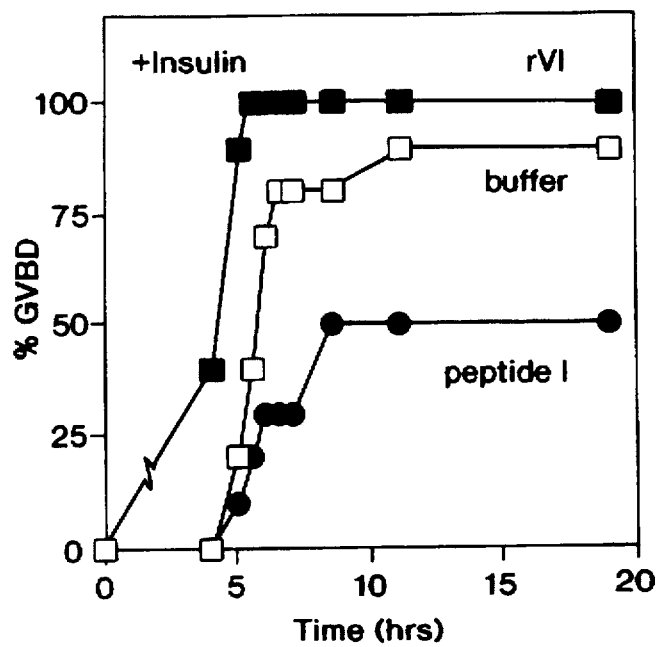
FIGS. 5A and 5B show the effects of peptides derived from RACK1 on PKC mediated maturation of Xenopus oocytes.
Figure 5B:
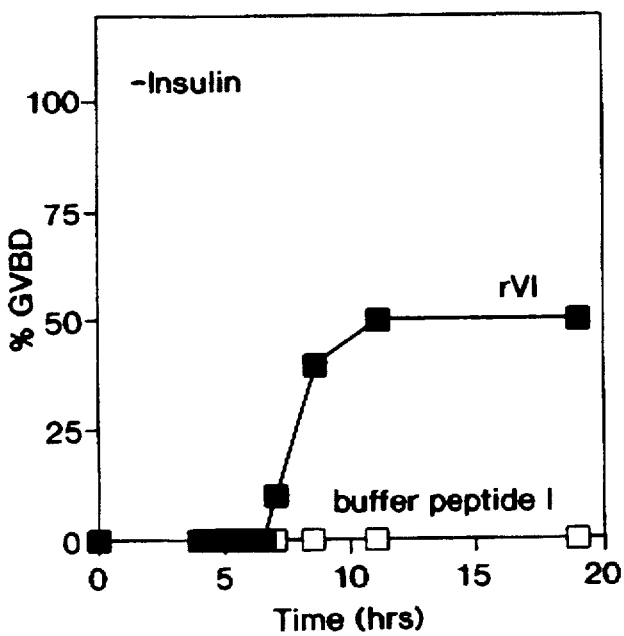

The *oocyte* maturation assay described above was also used to test the effect of various peptides derived from the PKC/RACK1 pair. Peptide I, derived from RACK1, as expected, inhibits the maturation of *Xenopus oocytes* presumably by interfering with the binding of βPKC1 to RACK1. On the other hand, a short peptide, rV1 derived from the sixth WD-40 repeat in RACK1 enhances maturation. Ron, D., Mochly-Rosen, D., *J Biol. Chem.* (1994) 269:21395–21398 This result is shown in FIG. 5. This peptide is believed to interfere with the RACK-mimicking site on PKC which normally covers the RACK-binding site in the absence of activation.

EXAMPLE 4

Figure 6:
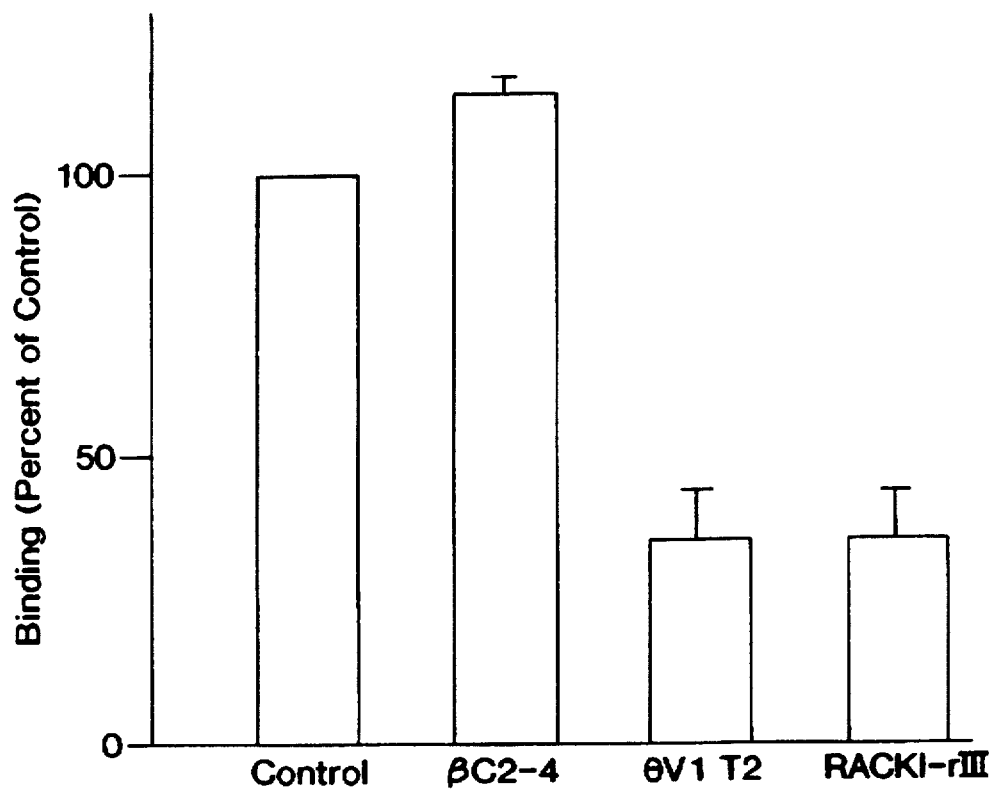
FIG. 6 shows the effect of various peptides on the binding of θPKC V1 fragment to RACK1 in vitro.

Interaction Peptides Derived from θPKC

θPKC is a member of the nPKC family and lacks a C2 region. Comparison of variable sequences of εPKC to other isozymes reveals regions of maximum disparity. Of these regions, some are strongly conserved across vast phylogenetic spans, e.g., from mammals to the invertebrate Aplysia. Isozyme specific sequences that are strongly conserved by evolution are probable sites for binding cognate proteins. Comparing δPKC to θPKC in the analogous region allowed identification of a θ-specific peptide expected to interfere with PKC binding to a RACK. Peptides with these characteristics from the V1 region of θPKC were prepared and tested for their ability to inhibit the binding of θPKC V1 fragment to RACK1 in vitro. The results are shown in FIG. 6. Of a multiplicity of peptides tested, both from other regions of the θPKC isoenzyme and from alternative isoenzymes in the family, only θV1 derived peptides θV1-1 and θV1-2, having the amino acid sequences GLSNFDCG (SEQ ID NO: 10) (θPKC residues 8–15) and YVESEN-GQMYI (SEQ ID NO: 11) (θPKC residues 36–46), respectively, were able to affect the interaction negatively. As expected, peptides rIII and rVI derived from the WD-40 regions of RACK1 were also effective.

Figure 11A:
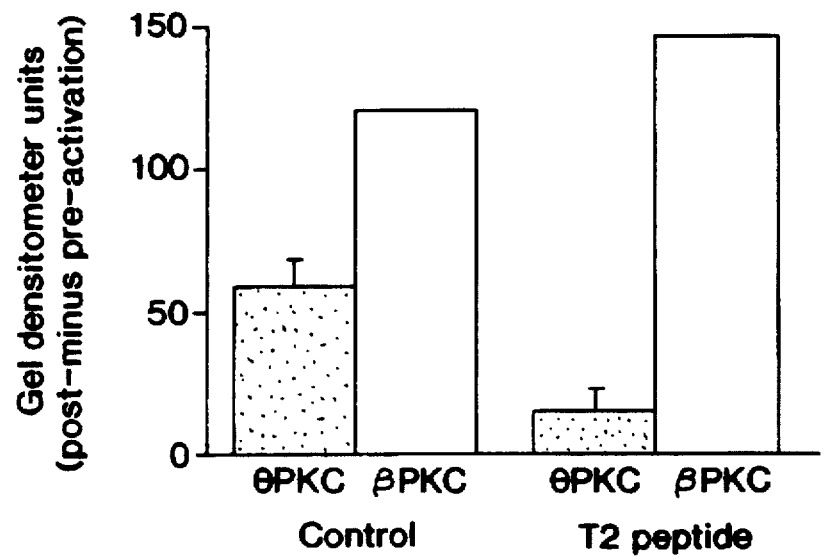
FIGS. 11A and 11B show that the T2 peptide (aa 36–46) from the V1 region of PKC-theta reduces translocation of PKC-theta, but not of PKC-beta, from the soluble to the particulate fraction after activation of JurkaT-cells with PMA/PHA (panel A); peptide is taken up spontaneously from the medium in JurkaT-cells. In parallel experiments, T2 peptide reduces expression of IL-2 as measured by ELISA in supernatant from stimulated cells (panel B).

The peptides θV1-1 and θV1-2 could inhibit the translocation of θPKC to the cellular particulate fraction in T-JurkaT-cells. The specificity of this interaction is shown in FIG. 11A which shows inhibition by the θPKC V1 peptide (T2) of the translocation of θPKC but not of βPKC.

Sequences derived from other PKC regions.

V3 region. The V3 or hinge region separates the regulatory and catalytic domains. This region contains the sites of proteolysis by trypsin and calpain. The lack of conservation of the V3 domain between the different PKC isozymes suggests that this section may also be at least, in part, involved in targeting the PKC isozymes to their anchoring proteins. Furthermore, it has been demonstrated that regions within the V3 of αPKC mediate the translocation of that isozyme to the nucleus (James G., and Olson E. J Cell Biol. 116:863–873, 1992). The V3 region of θPKC was found to bind to RACK1 in vitro. Therefore, the V3 region could affect not only the targeting of the activated isozymes (in which the V3-region is exposed) but could also regulate the enzyme susceptibilities to proteolysis.

V5. The amino acid sequences of the βPKC isoforms βIPKC and βIIPKC are identical except for variability within the V5 region (35 amino acids for βIPKC and 38 amino acids for βIIPKC). Upon activation, βIPKC and βIIPKC translocate to different localization sites in the cell (Disatnik M.-H., Buraggi G., Mochly-Rosen D. *Exp. Cell Res.* (1994) 210:287–297). This difference in localization of isozymes that are almost identical can be explained by the importance of the V5 region in mediating their targeting. Moreover, βIIPKC was found to selectively translocate to the nucleus upon proliferative stimulation where it selectively phosphorylated the nuclear envelope protein lamin B$_1$. (Murray N. R. Burns D. J. Fields A. P. (1994) *J Biol. Chem.* 269:1385–2191).

PKC-related proteins. Recently the human cDNAs encoding two novel protein kinases have been cloned. These proteins termed PRK1 and PRK2 (protein kinase C related kinase 1 and 2) show high homology to each other and some homology to the regulatory region of PKC (Palmer R. H., Ridden J., P. J. Parker *Eur. J Biochem.* (1995) 227:344–351. Since the sequences within the regulatory domain of PKC are responsible for the interaction between a PKC and its anchoring proteins, sequences from PRK1 and PRK2 which show homology to functionally important sequences within the regulatory domain of PKC, are likely to be of biological importance.

Sequences from other isozymes and related proteins that meet the same isozyme selectivity/evolutionary conservation criteria include the following:

Peptides derived from the V1 region of PKC isozymes (Human):

| Peptide | Sequence | Position |
|---|---|---|
| θV1-1 (SEQ ID NO:10) | G-L-S-N-F-D-C-G | θPKC(8–15) |
| θV1-2 (SEQ ID NO:11) | Y-V-E-S-E-N-G-Q-M-Y-I | θPKC(36–46) |
| θV1-3 (SEQ ID NO:12) | I-V-K-G-K-N-V-D-L-I | θPKC(73–82) |
| θV1-4 (SEQ ID NO:13) | D-M-N-E-F-E-T-E-G-F | θPKC(130–139) |
| δV1-1 (SEQ ID NO:14) | A-F-N-S-Y-E-L-G-S | δPKC(8–16) |
| δV1-2 (SEQ ID NO:15) | A-L-S-T-E-R-G-K-T-L-V | δPKC(35–45) |
| δV1-3 (SEQ ID NO:16) | V-L-M-R-A-A-E-E-P-V | δPKC(72–82) |
| δV1-4 (SEQ ID NO:17) | Q-S-M-R-S-E-D-E-A-K | δPKC(129–138) |
| εV1-1 (SEQ ID NO:18) | N-G-L-L-K-I-K | εPKC(5–11) |
| εV1-2 (SEQ ID NO:3) | E-A-V-S-L-K-P-T | εPKC(14–21) |
| εV1-3 (SEQ ID NO:19) | L-A-V-F-H-D-A-P-I-G-Y | εPKC(81–91) |
| εV1-4 (SEQ ID NO:20) | D-D-F-V-A-N-C-T-I | εPKC(92–100) |
| εV1-5 (SEQ ID NO:21) | W-I-D-L-E-P-E-G-R-V | εPKC(116–125) |
| εV1-6 (SEQ ID NO:22) | H-A-V-G-P-R-P-Q-T-F | εPKC(27–36) |
| εV1-7 (SEQ ID NO:23) | N-G-S-R-H-F-E-D | εPKC(108–115) |
| ηV1-1 (SEQ ID NO:24) | N-G-Y-L-R-V-R | ηPKC(9–15) |
| ηV1-2 (SEQ ID NO:25) | E-A-V-G-L-Q-P-T | ηPKC(18–25) |
| ηV1-3 (SEQ ID NO:26) | L-A-V-F-H-E-T-P-L-G-Y | ηPKC(84–94) |
| ηV1-4 (SEQ ID NO:27) | D-F-V-A-N-C-T-L | ηPKC(95–102) |
| ηV1-5 (SEQ ID NO:28) | W-V-D-L-E-P-E-G-K-V | ηPKC(120–129) |
| ηV1-6 (SEQ ID NO:29) | H-S-L-F-K-K-G-H | ηPKC(31–38) |
| ηV1-7 (SEQ ID NO:30) | T-G-A-S-D-T-F-E-G | ηPKC(111–119) |
| μV1-1 (SEQ ID NO:31) | M-S-V-P-P-L-L-R-P | μPKC(1–9) |
| μV1-2 (SEQ ID NO:32) | K-F-P-E-C-G-F-Y-G-L-Y | μPKC(86–96) |
| λV1-1 (SEQ ID NO:33) | H-Q-V-R-V-K-A-Y-Y-R | λPKC(15–24) |
| λV1-2 (SEQ ID NO:34) | Y-E-L-N-K-D-S-E-L-L-I | λPKC(87–94) |
| ζV1-1 (SEQ ID NO:35) | V-R-L-K-A-H-Y | ζPKC(16–22) |
| ζV1-2 (SEQ ID NO:36) | V-D-S-E-G-D | ζPKC(61–66) |
| ζV1-3 (SEQ ID NO:37) | V-F-P-S-I-P-E-Q | ζPKC(95–102) |

Peptides derived from the V3 region of PKC isozymes (Human):

| Peptide | Sequence | Position |
|---|---|---|
| δV3-1 (SEQ ID NO:38) | Q-G-F-E-K-K-T-G-V | δPKC(312–320) |
| δV3-2 (SEQ ID NO:39) | D-N-N-G-T-Y-G-K-I | δPKC(327–335) |
| εV3-1 (SEQ ID NO:40) | S-S-P-S-E-E-D-R-S | εPKC(336–344) |
| εV3-2 (SEQ ID NO:41) | P-C-D-Q-E-I-K-E | εPKC(351–358) |
| εV3-3 (SEQ ID NO:42) | E-N-N-I-R-K-A-L-S | εPKC(360–368) |
| εV3-4 (SEQ ID NO:43) | G-E-V-R-Q-G-Q-A | εPKC(393–400) |
| λV3-1 (SEQ ID NO:44) | M-D-Q-S-S-M-H-S-D-H-A-Q-T-V-I | λPKC(194–208) |
| λV3-2 (SEQ ID NO:45) | L-D-Q-V-G-E-E | λPKC(218–224) |
| λV3-3 (SEQ ID NO:46) | E-A-M-N-T-R-E-S-G | λPKC(227–234) |
| μV3-1 (SEQ ID NO:47) | D-P-D-A-D-Q-E-D-S | μPKC(390–398) |
| μV3-2 (SEQ ID NO:48) | S-K-D-T-L-R-K-R-H | μPKC(440–448) |
| μV3-3 (SEQ ID NO:49) | I-T-L-F-Q-N-D-T-G | μPKC(457–465) |
| μV3-4 (SEQ ID NO:50) | G-S-N-S-H-K-D-I-S | μPKC(559–567) |
| θV3-1 (SEQ ID NO:51) | C-S-I-K-N-E-A-R-L | θPKC(322–330) |
| θV3-2 (SEQ ID NO:52) | G-K-R-E-P-Q-G-I-S | θPKC(337–345) |
| θV3-3 (SEQ ID NO:53) | D-E-V-D-K-M-C-H-L | θPKC(351–359) |
| ζV3-1 (SEQ ID NO:54) | S-Q-E-P-P-V-D-D-K-N-E-D-A-D-L | ζPKC(194–208) |
| ζV3-2 (SEQ ID NO:55) | I-K-D-D-S-E-D | ζPKC(217–223) |
| ζV3-3 (SEQ ID NO:56) | P-V-I-D-G-M-D-G-I | ζPKC(226–234) |

-continued

| Peptide | Sequence | Position |
|---|---|---|
| βV3-1 (SEQ ID NO:57) | V-P-P-E-G-S-E-A | βPKC(290–297) |
| αV3-1 (SEQ ID NO:58) | I-P-E-G-D-E-E-G | αPKC(290–297) |
| γV3-1 (SEQ ID NO:59) | V-A-D-A-D-N-C-S | γPKC(290–297) |

Peptides derived from the V5 region of PKC isozymes (Human):

| Peptide | Sequence | Position |
|---|---|---|
| αV5-1(SEQ ID NO:60) | Q-L-V-I-A-N | αPKC(642–647) |
| βIV5-1(SEQ ID NO:61) | K-L-F-I-M-N | βIPKC(646–651) |
| βIIV5-1(SEQ ID NO:62) | Q-E-V-I-R-N | βIIPKC(645–650) |
| δV5-1(SEQ ID NO:63) | K-N-L-I-D-S | δPKC(649–654) |
| εV5-1(SEQ ID NO:64) | E-A-I-V-K-Q | εPKC(714–719) |
| ηV5-1(SEQ ID NO:65) | E-G-H-L-P-M | ηPKC(657–662) |
| λV5-1(SEQ ID NO:66) | D-D-I-V-R-K | λPKC(559–564) |
| μV5-1(SEQ ID NO:67) | S-D-S-P-E-A | μPKC(898–903) |
| θV5-1(SEQ ID NO:68) | R-A-L-I-N-S | θPKC(680–685) |
| ζV5-1(SEQ ID NO:69) | E-D-A-I-K-R | ζPKC(556–561) |

Peptides derived from protein kinase C related proteins (Human):

| Peptide | Sequence | Position |
|---|---|---|
| PRK1-1(SEQ ID NO:70) | Q-D-S-K-T-K-I-D | PRK1(171–178) |
| PRK2-1(SEQ ID NO:71) | Q-D-S-K-T-K-I-E | PRK2(181–188) |
| PRK1-2(SEQ ID NO:72) | E-L-A-V-F-W-R-D | PRK1(430–437) |
| PRK2-2(SEQ ID NO:73) | E-I-S-V-Y-W-R-D | PRK2(432–439) |
| PRK1-3(SEQ ID NO:74) | M-E-P-Q-G-C-L | PRK1(465–471) |
| PRK2-3(SEQ ID NO:75) | L-E-P-Q-G-T-L | PRK1(467–473) |

μV1-1, μV1–2 derived from μPKC were picked because they aligned with εV1–2 and θV1–2 and part of θV1–1 respectively. λV1–1 and λV1–2 from λPKC were picked based on their alignment with εV1–2 and part of εV1–3 and θV1–2 respectively. ζV1- 1, ζV1–2, ζV1–3 derived from ζPKC were picked according to their homology to: εV1–2, εV1–2, and εV1–3 respectively. PRK1-1and PRK2-2 were identified according to their homology to βC2-1. PRK1–2 and PRK2-2 were identified according to their homology to the biologically active εPKC-derived peptide εV1-3 and part of εV1-2. PRK1–3 and PRK2–3 were picked according to their alignment with the peptide εV1-5.

The peptide sequences were generated by aligning the human PKC sequences and the human PRK1 and PRK2 sequences using the MegAlign DNASTAR Inc. program. The sequences were aligned by using the clustal method. The algorithm groups sequences into clusters by examining the distances between all pairs. The clusters are aligned, first individually, then collectively to produce an overall alignment. (Higgins D. G. and Sharp, P. M. (1989). CABIOS, Vol 5, No 2, 151–153). The matrix for the alignment was PAM250 (percent accepted mutation 250-2.5 mutations per residue). This matrix allows only high stringency alignments.

EXAMPLE 5

In this example, evidence is provided which identifies a specific protein as a cognate binding partner to PKC-theta in T-cells. This protein is a tyrosine protein kinase called fyn, which was previously known and believed to play an important role in T-cell function. Evidence is further provided to demonstrate that disrupting the localization of PKC-theta, using peptides from the PKC domain which interacts with fyn, depresses T-cell function.

The T-cell Receptor is associated with (at minimum) the CD3 and CD4 complexes of proteins, to which several tyrosine kinases are associated at low stoichiometry; PLC-gamma, important in generating second messengers such as diacylglycerol and inositol triphosphate, is also a substrate for tyrosine phosphorylation. Among the non-receptor tyrosine kinases are ZAP-70 and the src-related proteins fyn and lck, believed to interact with CD3 and CD4 respectively; another tyrosine kinase, csk, is also associated with the TCR supercomplex of proteins.

In some reports, fyn is only included in 1% of the CD3 complexes. A transient association makes sense, however, in the context of what is known about other localization factors, such as RACK1 for PKC, which are similarly present in particular places in the cell only during particular signal transduction episodes. A role for fyn in T-cell signaling is well documented, including association with at least half a dozen other proteins which are also associated under some experimental conditions with TCR (Penninger et al., Immunol. Rev. 135:183–214 (1993). An association of fyn with PKC has not been previously observed.

The evidence that fyn interacts with PKC-theta comes from several independent and mutually supportive lines of experimentation. In most cases, the region of PKC-theta used to define the binding specificity was the V1 region (~140 amino acids), which is from the regulatory domain of PKC and is a sequence unique to this isozyme; some experiments also used the V3 domain. FIG. 1. Proteins that interact with these regions fulfill the criteria defined in Examples 1–4. In the data provided in Example 1–4, RACK1 was shown to have some degree of binding to PKC-theta, which could be partially blocked with the T1 or T2 peptides (derived from the V1 region). Both peptides were also able to inhibit normal subcellular translocation of PKC-theta following treatment with activators of the signal transduction network; the latter experiments indicate the importance of the V1 region but do not suffice to identify the physiologically relevant cognate binding partner.

To identify the physiologically relevant cognate binding partner, a Triton (non-ionic detergent) cell extract was prepared from JurkaT-cells (a human T-cell lymphoma line) using standard procedures. Based on the prior experience that physiologically relevant cognate binding partners for PKC may be associated with the particulate fraction, the Triton extract included both soluble and some particulate fraction proteins and is referred to herein as the Triton extract. A V1-his tail construct was also engineered; the V1 sequence was attached at the N-terminus to six histidine residues. The six histidine residues bind to Nickel agarose affinity beads.

Figure 7A:
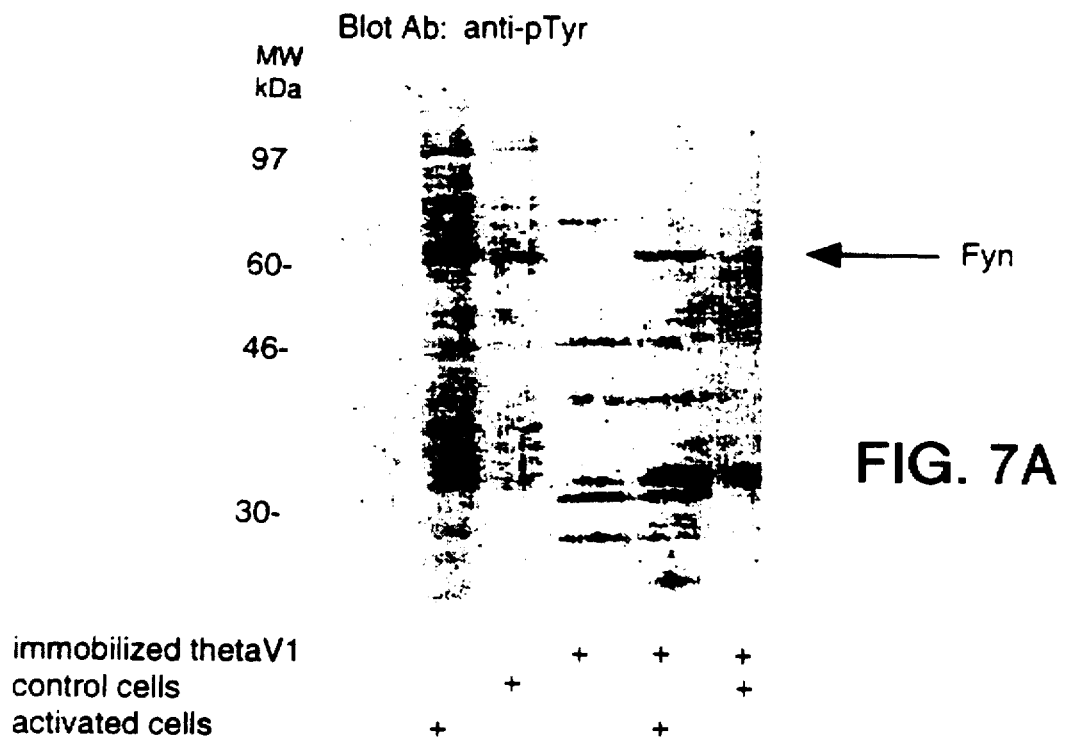
FIGS. 7A and 7B are photocopies of immunoblots. A Triton extract of JurkaT-cells was incubated with V1 immobilized on the affinity beads. After washing, the bound proteins were separated by electrophoresis and blotted to a membrane. Probing such a blot with antibodies to phosphotyrosine (panel A) reveals several bands, including a prominent band at ~60 kDa. In panel B, a band of the same approximate MW is visualized with an antibody to the tyrosine kinase fyn.
Figure 7B:
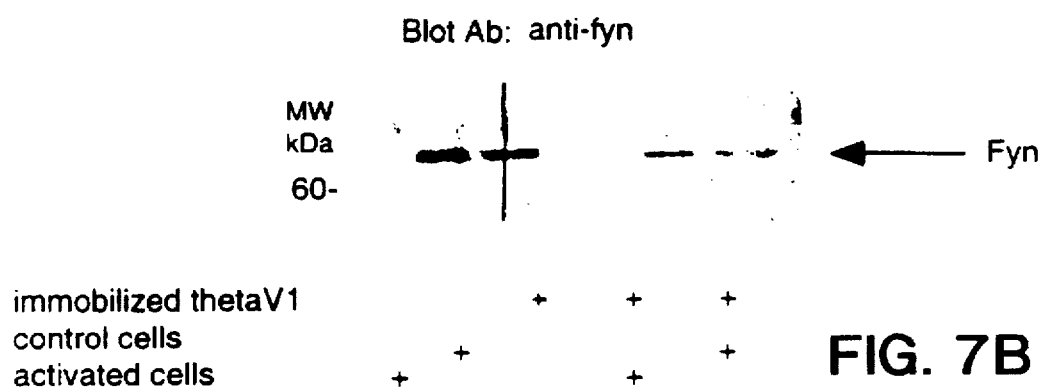

Using these beads as an affinity extraction medium, the V1 region was immobilized and incubated with the Triton extract. After washing (by centrifugation in an Eppendorf tube), the bound proteins were eluted with strongly denaturing SDS gel sample buffer. After the eluate was separated by gel electrophoresis and transferred to a membrane, fyn was detectable using a fyn specific antibody (Santa Cruz Biotechnology, Santa Cruz, Calif.) (FIG. 7B). A band at the same molecular weight was also detected by antibodies to phosphotyrosine (Transduction Laboratories, Lexington, Ky. (FIG. 7A). Antibodies to a related tyrosine kinase, csk, did not indicate any binding to the PKC domain.

Figures 8A, 8B:
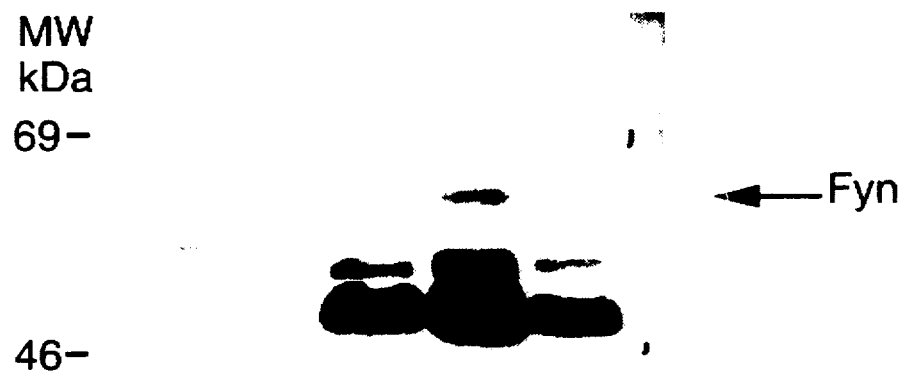
FIGS. 8A and 8B are photocopies of immunoblots which show that antibodies prepared against the V1 variable region of PKC-theta were used to immunoprecipitate the PKC and any bound proteins in a JurkaT-cell extract. After electrophoresis and blotting to a membrane, the precipitated proteins were visualized with antibodies to phosphotyrosine and to ton; the arrows identify the MW positions for fyn .

Antibodies prepared against the V1 (isozyme specific) region of PKC-theta were used to immunoprecipitate PKC-theta and any associated proteins from the particulate fraction (overnight at 4°). These associated proteins were separated by gel electrophoresis and blotted to a membrane. When such a blot was probed with an antibody against phosphotyrosine, several bands were identified including a prominent one at the MW of fyn , 59 kDa, FIG. 8A. By contrast, a band at the MW of lck was not identified. Direct evidence that the coprecipitated protein is fyn was provided by staining with a commercially available labeled antibody prepared against fyn, FIG. 8B. As a control for specificity, antibodies to PKC-beta were successfully used to coprecipitate RACK1, the known cognate binding protein for this isozyme; fyn was not coprecipitated in this case.

To define the fyn subsequence specificity of interaction, a modified yeast two hybrid system was used (U.S. Pat. No. 5,283,173, Vojtek et al. Cell 74:205–214 (1993). Gene sequences for PKC-theta V1 and fyn were cloned as fusions to complementing halves of a transcription factor. In the particular system used, two reporter genes become activated as a consequence of the association between the two hybrid proteins, which thereby restores the holoenzyme status of the transcriptional activator. The first reporter is a histidine auxotroph repair enzyme, allowing growth selection; the second is beta-galactosidase, whose activity can be visualized with the substrate x-gal which turns blue following enzymatic cleavage. Visual inspection of the colonies allows scoring of interactions as strong (full color development within 2 hours), weak (by 12 hours), null (no signal at 24 hours).

The catalytic domain and the regulatory domain of fyn were therefore tested separately as binding partners to the V1 region of PKC-theta. The catalytic domain gave a strong signal, and the regulatory domain gave a medium signal. It is not known if each domain folds equally well into a stable structure, so this difference is not conclusive as to what portion of fyn has the best binding to V1. The V3 region of PKC-theta has also been tested against the fyn regulatory, and catalytic domain constructs; both interact as measured by his selection, with beta-galactosidase experiments all showing strong interaction. It thus appears that PKC-theta interacts with fyn over a substantial contact surface. In contrast to the coprecipitation experiments using antibodies to the V1 region, antibodies to the V3 region failed to immunoprecipitate fyn, suggesting that the V3 antibodies and fyn are binding in part to the same site.

To test the specificity of the interaction of PKC-theta V1 with the fyn domains as compared to other proteins, the two hybrid system constructs incorporating the fyn portions were diluted into a large excess of random cDNA clones in the analogous vector. For the kinase domain, 10 of 12 positive clones picked at random were the fyn construct which had been spiked into the library; for the regulatory domain, 3 of 6 were from the spiked fyn construct. The cDNA library was prepared from murine T-cells and it remains to be determined if the other positive clones represent the murine equivalent of fyn . The interaction of PKC-theta withfin appears to be specific since an analogous construct using the V1 region of the most closely related isozyme, PKC-delta, did not appear to bind to fyn. FIG. 1 and 9A summarizes the gene constructs used and FIG. 9B provides the interaction data obtained.

It is possible that PKC binds at the interface between the two fyn domains, which are both exposed upon activation. A PKC consensus phosphorylation site has been identified within the primary sequence of fyn, centered on threonine-297, in a short stretch of sequence that also scores high as part of an ATP binding consensus site. It is known that fyn has alternative splicing forms; the form found in T-cells includes the consensus PKC site, although this site is not unique to T-cells. Interestingly, addition of ATP to JurkaT-cell extracts reduces the association of PKC-theta and fyn, measured by immunoprecipitation further suggesting a physiological interaction between the two proteins. By weaker criteria for a PKC consensus site, fyn has 13 additional potential phosphorylation sites. Finally, it is further possible that PKC is a substrate for fyn, since there are 5 tyrosine residues in the V1 region; tyrosine-36 looks particularly reasonable in this regard.

The first PKC cognate binding protein, RACK1, was a clear member of the WD40 family of proteins, characterized by having multiple tandem copies of a sequence of ~40 amino acids with a conserved WD pair towards the C-terminus. Fyn also has three repeats with weak WD40 homology (aa 51–270), beginning in the middle of the Unique region and ending early in the catalytic domain. At a more detailed level, RACK1 shares several other short sequences of homology with fyn, both in its regulatory and catalytic domains.

Since fyn has an SH3 domain, other homologs of which are known to bind proline rich domains, it is noteworthy that PKC-theta has a moderately proline rich region of ~50 residues (includes 10 prolines), accounting for a substantial part of the V3 region. Antibodies to the V3 region failed to immunoprecipitate fyn, suggesting that the antibody and fyn are binding in part to the same site. These results are not conclusive since the V3 region gave positive results in the two-hybrid system. Most other PKC isozymes do not contain proline rich regions, including the most closely related isozyme PKC-delta. The only other isozyme in which a moderately proline rich domain is found is PKC-mu, a recently described member of the class with much less homology to theta than delta, FIG. 10 for sequence motifs.

In summary, the key independent lines of evidence indicating that fyn is a physiologically relevant binding partner for PKC-theta in T-cells are: (i) a PKC-theta variable domain pulls fyn out of a cell extract in an affinity binding mode; (ii) antibodies to PKC-theta variable domain immunoprecipitate a complex of PKC and fyn from cell extracts; (iii) PKC-theta variable domains and fyn interact in the yeast two hybrid system. In all cases, appropriate controls using closely related proteins show specificity of the interaction.

The existence of cognate binding proteins has been previously described, as have methods for their identification and their utility in drug discovery (for example see Fields, U.S. Pat. No. 5,283,173 and U.S. Pat. No. 5,352,660). The actual identification of fyn as a partner for PKC-theta can now be used in such art known methods to identify and isolate compounds which block fyn/PKC-theta interactions. Such agents can be used to modulate biological activities which are mediated by fyn/PKC-theta binding.

Figure 11B:
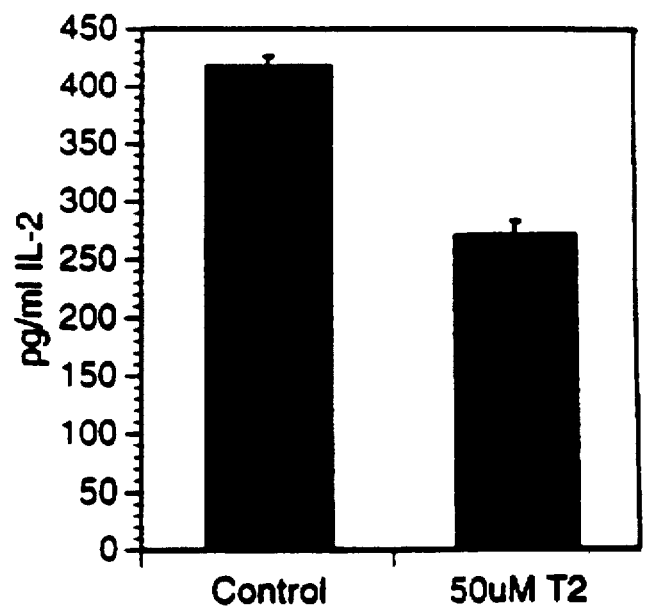

We have observed that the T2 peptide, which blocks PKC-theta translocation (FIG. 7) and hence blocks association with the cognate localization factor, causes measurable suppression of IL-2 production from activated JurkaT-cells, FIG. 11.

What is claimed is:

1. A method for identifying compounds which reduce human fyn/PKC-theta binding, said method comprising the steps of:

a) mixing i) human PKC-theta, a cell or virus expressing hman PKC-theta, a fragment of human PKC-theta containing the fyn binding site, or a cell or virus expressing a fragment of human PKC-theta containing the fyn binding site, and ii) the human fyn protein, or a cell or virus expressing the human fyn protein, a fragment of the human fyn protein which contains the PKC-theta binding site, or a cell or virus expressing a fragment of the human fyn protein containing PKC-theta binding site, in the presence and absence of a candidate compound;

b) determining whether the presence of the candidate compound reduces the binding of the PKC-theta to the fyn;

c) identifying a compound which reduces the binding of human fyn to human PKC-theta.

2. The method of claim 1, wherein said method is performed using the complete fyn protein.

3. The method of claim 1, wherein said method is performed using a fragment of the fyn protein, wherein said fragment contains the PKC-theta binding site.

4. The method of claim 1, wherein said method is performed using human PKC-theta.

5. The method of claim 1 wherein said method is performed using a fragment of the PKC-theta protein, wherein said fragment contains the fyn binding site.

6. The method of claim 1 wherein said method is performed using a cell or virus expressing said PKC-theta or fyn or fragments thereof.

7. The method of claim 1, wherein one or both of said PKC-theta or fyn proteins, or fragments thereof, is provided as a fusion protein.

8. The method of claim 1, wherein one or both of said PKC-theta or fyn proteins, or fragments thereof, are detectably labeled.

9. The method of claim 1, wherein one or both of said PKC-theta or fyn proteins, or fragments thereof, are immobilized on a solid support.

10. The method of claim 1 wherein said candidate compound is first tested for the ability to bind to PKC-theta, or a fragment of PKC-theta containing the fyn binding site.

11. The method of claim 1 wherein said candidate compound is first tested for the ability to bind to fyn, or a fragment of fyn containing the PKC-theta binding site.

* * * * *